United States Patent
Ober et al.

(10) Patent No.: US 9,246,108 B2
(45) Date of Patent: Jan. 26, 2016

(54) QUINOLINE-BENZOXAZOLE DERIVED COMPOUNDS FOR ELECTRONIC FILMS AND DEVICES

(71) Applicant: Dow Global Technologies LLC, Midland, MI (US)

(72) Inventors: Matthias S. Ober, Midland, MI (US); Robert D. Froese, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 133 days.

(21) Appl. No.: 13/828,470

(22) Filed: Mar. 14, 2013

(65) Prior Publication Data
US 2014/0183413 A1 Jul. 3, 2014

Related U.S. Application Data

(60) Provisional application No. 61/746,748, filed on Dec. 28, 2012.

(51) Int. Cl.
| | |
|---|---|
| H01B 1/12 | (2006.01) |
| H01L 51/00 | (2006.01) |
| C09K 11/06 | (2006.01) |
| C07D 413/14 | (2006.01) |
| C07D 413/04 | (2006.01) |
| H01L 51/50 | (2006.01) |

(52) U.S. Cl.
CPC .......... *H01L 51/0071* (2013.01); *C07D 413/04* (2013.01); *C07D 413/14* (2013.01); *C09K 11/06* (2013.01); *C09K 2211/1029* (2013.01); *C09K 2211/1033* (2013.01); *H01L 51/0072* (2013.01); *H01L 51/0077* (2013.01); *H01L 51/0081* (2013.01); *H01L 51/5012* (2013.01); *H01L 51/5056* (2013.01); *H01L 51/5072* (2013.01)

(58) Field of Classification Search
CPC .............................. H01L 51/0071; H01B 1/12
USPC ........................................... 252/500; 546/167
See application file for complete search history.

(56) References Cited

U.S. PATENT DOCUMENTS

| | | | |
|---|---|---|---|
| 3,840,552 A * | 10/1974 | Harnisch ....................... 548/224 |
| 3,959,306 A * | 5/1976 | Harnisch .................... 548/305.1 |
| 4,016,172 A * | 4/1977 | Harnisch ....................... 548/224 |
| 4,948,900 A | 8/1990 | Iijima et al. |
| 5,057,526 A | 10/1991 | von der Saal et al. |
| 5,462,694 A | 10/1995 | Kosaka et al. |
| 5,494,918 A | 2/1996 | Neuenschwander et al. |
| 5,523,312 A | 6/1996 | Aldous et al. |
| 5,641,427 A | 6/1997 | Shinjo et al. |
| 5,653,913 A | 8/1997 | Nakamura et al. |
| 5,868,960 A | 2/1999 | Kosaka et al. |
| 7,262,204 B2 | 8/2007 | Collins et al. |
| 7,622,479 B2 | 11/2009 | Oda et al. |
| 8,039,505 B2 | 10/2011 | Trede |
| 2004/0224977 A1 | 11/2004 | Walker et al. |
| 2005/0101647 A1* | 5/2005 | Oda et al. ...................... 514/367 |
| 2009/0163545 A1* | 6/2009 | Goldfarb ....................... 514/312 |
| 2010/0093703 A1 | 4/2010 | Wagner et al. |
| 2010/0210594 A1 | 8/2010 | Wagner et al. |
| 2011/0081428 A1 | 4/2011 | Lithgow et al. |
| 2012/0101096 A1 | 4/2012 | Hedstrom et al. |
| 2012/0214994 A1 | 8/2012 | Chi et al. |

FOREIGN PATENT DOCUMENTS

| | | |
|---|---|---|
| JP | 03258770 | 11/1991 |
| JP | 05194222 | 8/1993 |
| JP | 09110856 | 4/1997 |
| JP | 2000017261 | 1/2000 |
| JP | 2000191657 A | 7/2000 |
| JP | 2005060367 | 3/2005 |
| JP | 2011168515 | 1/2011 |
| KR | 20090131958 | 12/2009 |
| WO | 9730119 A1 | 8/1997 |
| WO | 0216333 A2 | 2/2002 |
| WO | 2008073451 A2 | 6/2008 |
| WO | 2009021750 A2 | 2/2009 |
| WO | WO 2009021750 A2 * | 2/2009 ........... C07D 413/04 |
| WO | 2010112093 A1 | 10/2010 |

OTHER PUBLICATIONS

Chau Ming So et al., "Palladium-Catalyzed Direct Arylation of Heteroarenes with Aryl Mesylates", Chem. Eur. J., 2011, 17, 761-765.*
CAS reg. No. 1616593-22-6, Jul. 22, 2014.*
CAS reg. No. 1616593-21-5, Jul. 22, 2014.*
CAS reg. No. 1616593-20-4, Jul. 22, 2014.*
CAS reg. No. 537027-48-8, Jun. 25, 2003.*

* cited by examiner

Primary Examiner — Douglas Mc Ginty

(57) ABSTRACT

The invention provides a composition comprising at least one compound selected from the following Formulas A, B1, B2, B3, B4 or C:

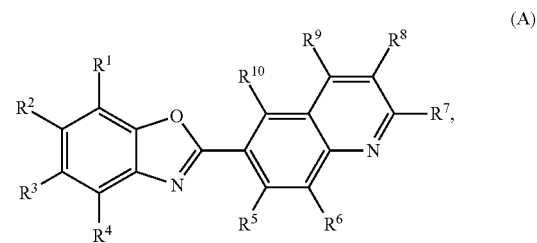

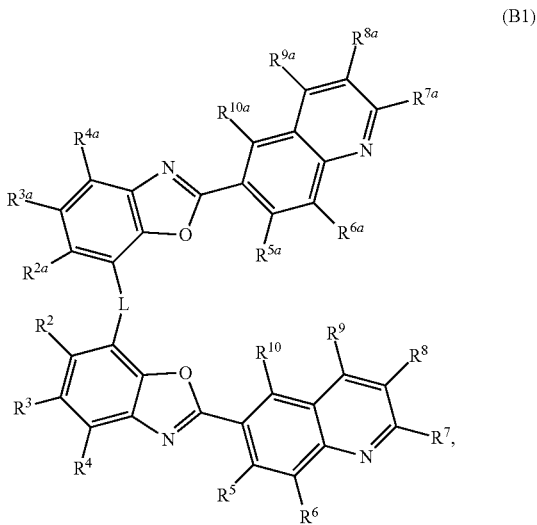

-continued
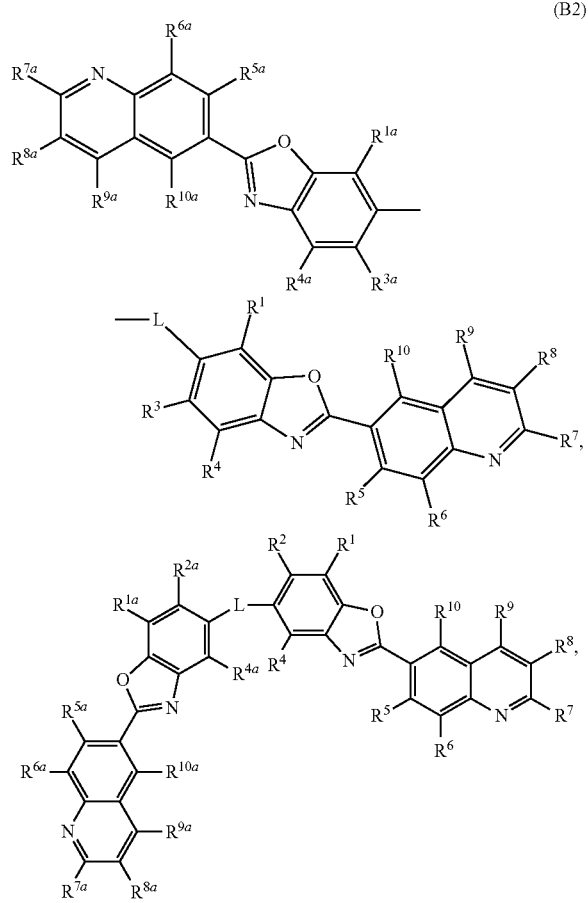
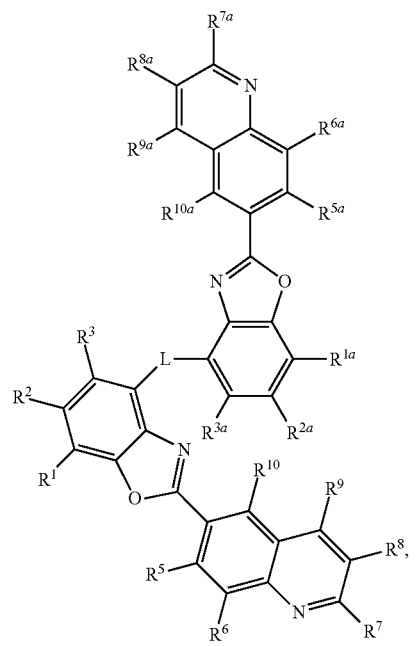
or a combination thereof (C). For each formula, the R groups are described herein.
15 Claims, No Drawings

QUINOLINE-BENZOXAZOLE DERIVED COMPOUNDS FOR ELECTRONIC FILMS AND DEVICES

REFERENCE TO RELATED APPLICATIONS

This application claims the benefit of U.S. Provisional Application No. 61/746,748, filed on Dec. 28, 2012.

BACKGROUND

Organic light emitting devices (OLEDs) are devices, in which the electroluminescent layer is a film containing at least one organic compound that emits light in response to an electric current. Most OLEDs consist of a stack of different aromatic compounds with well-defined HOMO and LUMO levels. Such compounds are generally classified as electroluminescent materials and charge transport materials. Several properties required for such electroluminescent and charge transport compounds include high fluorescent quantum yield in solid state, high mobility of electrons and holes, chemical stability during vapor-deposition in vacuum, and the ability to form stable films. Common problems with OLEDs include fast aging/short life span, undesirably high operating voltages, or insufficient efficiency. Thus, here is a need for new compounds for OLED devices that enable long-lasting and highly efficient devices. Compounds with these characteristics typically require specific HOMO and LUMO energy levels, and a sufficient energy gap between HOMO and LUMO. Furthermore, compounds with high triplet energies are particularly desirable to support phosphorescent emitters.

KR2009131958A (Abstract) discloses a diverse set of aromatic compounds, including a specific 2-(quinoline-6-yl)-benzoxazole example for use in organic photoelectric devices. Such compounds are disclosed as having an inherent dipole moment, which leads to an improvement in charge mobility and various optical properties, and are disclosed as having lifetime, efficiency, thermal and electrochemical stability.

Other quinoline-benzoxazole compounds are disclosed in the following references. EP1460067A1; JP2011168515A (Abstract); JP2000017261A (Abstract); JP2000191657 (Abstract); US20110081428; WO2009021750; WO2008073451; WO2002016333; WO1996009822; EP694599A2; EP641850A1; EP640676A1; EP640677A1; and WO1992015579. However, as discussed above, there remains a need for new compounds for OLED devices that enable long-lasting and highly efficient devices, and which are suitable for use both with fluorescent and phosphorescent emitters. These needs and others have been met by the following invention.

SUMMARY OF INVENTION

The invention provides a composition comprising at least one compound selected from the following Formulas A, B1, B2, B3, B4 or C:

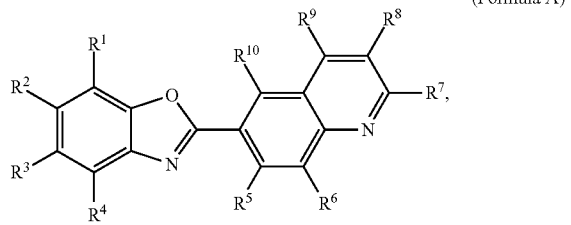

(Formula A)

A)
wherein R1, R2, R3, R4, R5, R6, R7, R8, R9 and R10 are each, independently, selected from the following: a) hydrogen atom; b) a deuterium atom; c) a (C1-C30) alkyl group; d) a substituted (C1-C30) alkyl group; e) a (C6-C50) aryl group; f) a substituted (C6-C50) aryl group; g) a (C3-C50) heteroaryl group; h) a substituted (C3-C50) heteroaryl group; i) a (C3-C30) cycloalkyl group; j) a substituted (C3-C30) cycloalkyl group; or k) a group represented by —(Ar$_1$)$_m$—(Ar$_2$), wherein Ar$_1$ is selected from the group consisting of the following: a substituted or unsubstituted (C5-C30) arylene group, and a substituted or unsubstituted (C5-C30) heteroarylene group, and Ar$_2$ is selected from the group consisting of the following: a substituted or unsubstituted (C5-C30) aryl group, a substituted or unsubstituted (C5-C30) aryloxy group, and a substituted or unsubstituted (C4-C30) heteroaryl group.

m is an integer from 0 to 5, and

—(Ar$_1$)$_m$— groups in —(Ar$_1$)$_m$—(Ar$_2$) are identical or different from one another;

and with the proviso that at least one of R1, R2, R3, and R4 comprises at least 10 carbon atoms and one cyclic aromatic ring;

and wherein, optionally, two or more R groups selected from R1, R2, R3, R4, R5, R6, R7, R8, R9 and R10 may form one or more ring structures;

and with the proviso that none of R1, R2, R3, R4, R5, R6, R7, R8, R9 and R10 comprise a hydroxyl, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety;

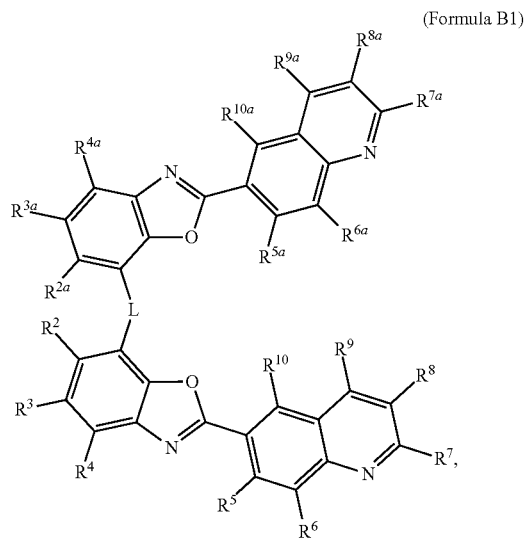

(Formula B1)

B1)
wherein R2, R3, R4, R5, R6, R7, R8, R9, R10, R2a, R3a, R4a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and wherein, optionally, two or more R groups selected from R2, R3, R4, R5, R6, R7, R8, R9 and R10 may form one or more ring structures;

and wherein, optionally, two or more R groups selected from R2a, R3a, R4a, R5a, R6a, R7a, R8a, R9a and R10a may form one or more ring structures;

and with the proviso that none of R2, R3, R4, R5, R6, R7, R8, R9, R10, R2a, R3a, R4a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom;

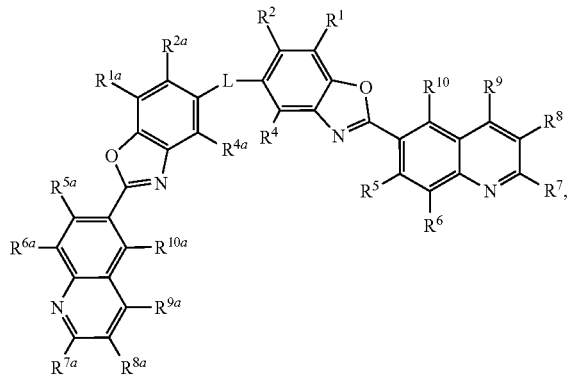

(Formula B3)

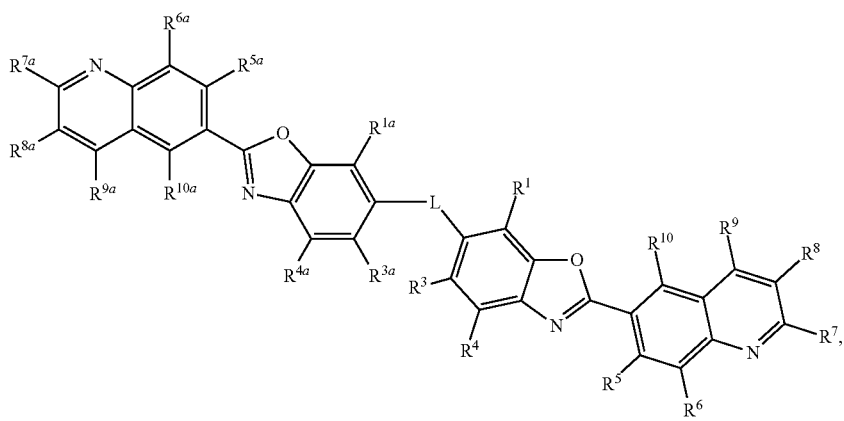

(Formula B2)

B2)

wherein R1, R3, R4, R5, R6, R7, R8, R9, R10, R1a, R3a, R4a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and wherein, optionally, two or more R groups selected from R1, R3, R4, R5, R6, R7, R8, R9 and R10 may form one or more ring structures;

and wherein, optionally, two or more R groups selected from R1a, R3a, R4a, R5a, R6a, R7a, R8a, R9a and R10a may form one or more ring structures;

and with the proviso that none of R1, R3, R4, R5, R6, R7, R8, R9, R10, R1a, R3a, R4a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom;

B3)

wherein R1, R2, R4, R5, R6, R7, R8, R9, R10, R1a, R2a, R4a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and wherein, optionally, two or more R groups selected from R1, R2, R4, R5, R6, R7, R8, R9 and R10 may form one or more ring structures;

and wherein, optionally, two or more R groups selected from R1a, R2a, R4a, R5a, R6a, R7a, R8a, R9a and R10a may form one or more ring structures;

and with the proviso that none of R1, R2, R4, R5, R6, R7, R8, R9, R10, R1a, R2a, R4a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom;

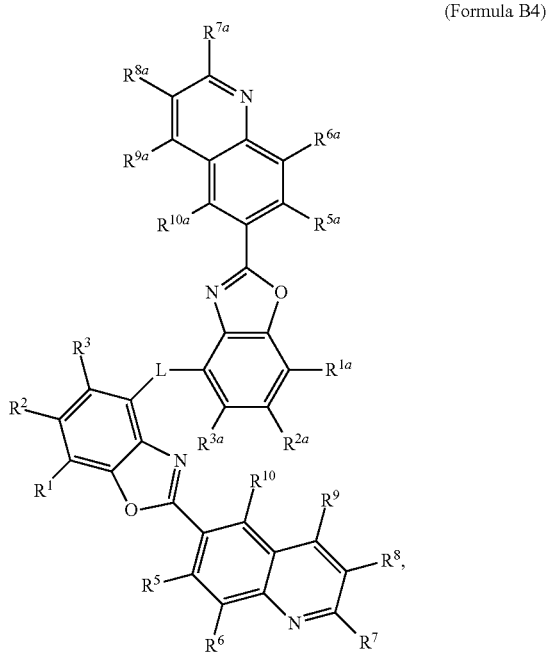

(Formula B4)

B4)
wherein R1, R2, R3, R5, R6, R7, R8, R9, R10, R1a, R2a, R3a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and wherein, optionally, two or more R groups selected from R1, R2, R3, R5, R6, R7, R8, R9 and R10 may form one or more ring structures;

and wherein, optionally, two or more R groups selected from Ra1, R2a, R3a, R5a, R6a, R7a, R8a, R9a and R10a may form one or more ring structures;

and with the proviso that none of R1, R2, R3, R5, R6, R7, R8, R9, R10, R1a, R2a, R3a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom; or C) a combination thereof.

DETAILED DESCRIPTION

New compounds for electronic films and devices, such as OLEDs, have been discovered. Such compounds have suitable HOMO and LUMO levels, a suitable energy gap between HOMO and LUMO, high triplet energies, low current densities and high luminous efficiencies. The inventive compounds also have suitable CLogP values for such films and devices. Higher CLogP values tend to correlate with lower heteroatom- and functional group densities (especially acidic functional groups) for a given molecular weight; and molecules devoid of such features tend to exhibit better temperature stabilities.

As discussed above, the invention provides a composition comprising at least one compound selected from the following Formulas A, B1, B2, B3, B4 or C:

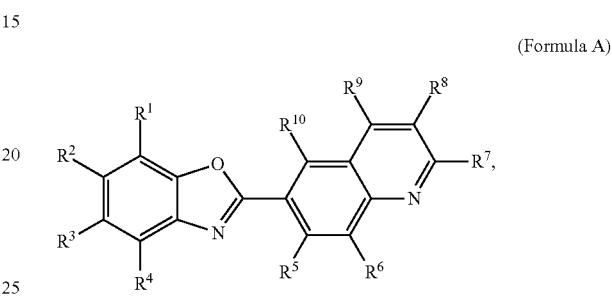

(Formula A)

A)
wherein R1, R2, R3, R4, R5, R6, R7, R8, R9 and R10 are described above;

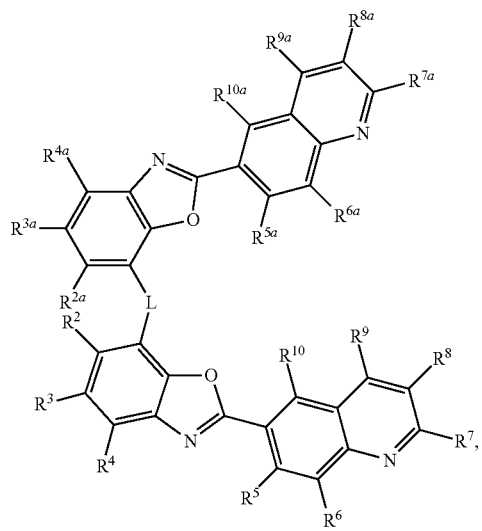

(Formula B1)

B1)
wherein R2, R3, R4, R5, R6, R7, R8, R9, R10, R2a, R3a, R4a, R5a, R6a, R7a, R8a, R9a, and R10a are described above;

(Formula B2)

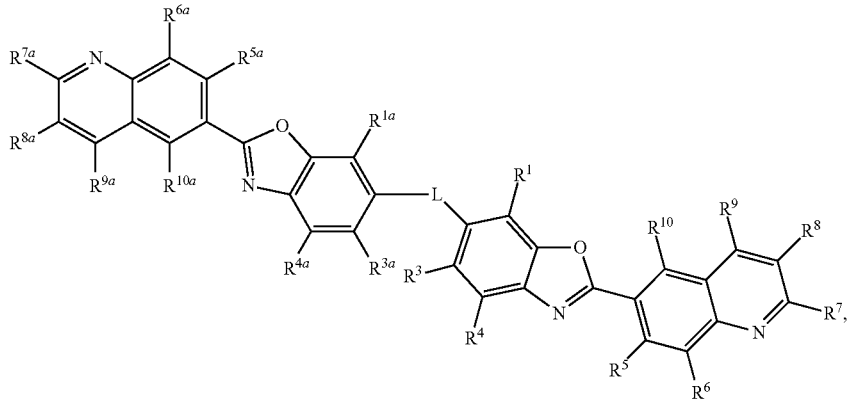

B2)
wherein R1, R3, R4, R5, R6, R7, R8, R9, R10, R1a, R3a, R4a, R5a, R6a, R7a, R8a, R9a, and R10a are described above;

(Formula B3)

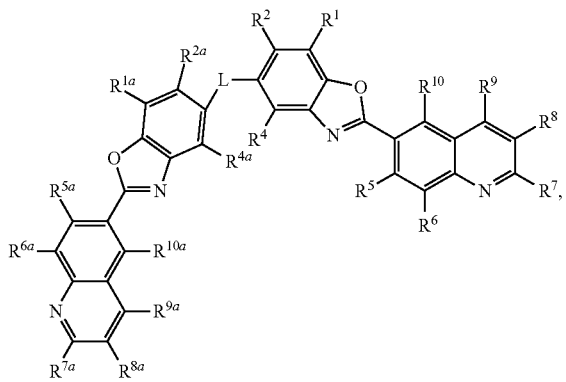

B3)
wherein R1, R2, R4, R5, R6, R7, R8, R9, R10, R1a, R2a, R4a, R5a, R6a, R7a, R8a, R9a, and R10a are described above;

(Formula B4)

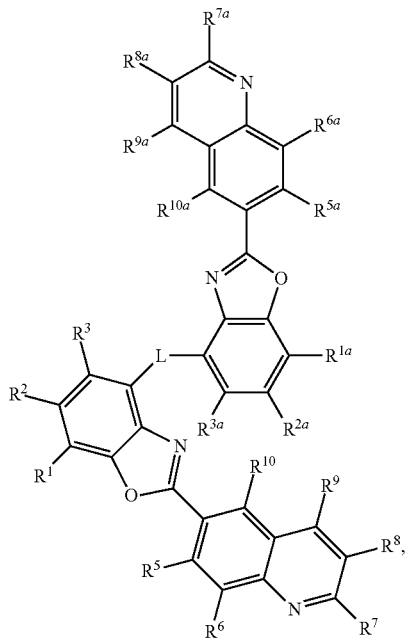

B4)
wherein R1, R2, R3, R5, R6, R7, R8, R9, R10, R1a, R2a, R3a, R5a, R6a, R7a, R8a, R9a, and R10a are described above; or C) a combination thereof.

An inventive composition may comprise a combination of two or more embodiments described herein.

An inventive compound of Formula A, B1, B2, B3 or B4 may comprise a combination of two or more embodiments described herein.

As used herein R1=$R^1$, R2=$R^2$, R3=$R^3$, and so forth. As used herein R1a=$R^{1a}$, R2a=$R^{2a}$, R3a=$R^{3a}$, and so forth.

In one embodiment, for Formula A, R1, R2, R3, R4, R5, R6, R7, R8, R9 and R10 are each, independently, selected from the following: a) hydrogen atom; b) a deuterium atom; c) a (C1-C30) alkyl group; d) a substituted (C1-C30) alkyl group; e) a (C6-C50) aryl group; f) a substituted (C6-C50) aryl group; g) a (C3-C50) heteroaryl group; h) a substituted (C3-C50) heteroaryl group; i) a (C3-C30) cycloalkyl group; j) a substituted (C3-C30) cycloalkyl group; or k) a group represented by —$(Ar_1)_m$—$(Ar_2)$, wherein $Ar_1$ is selected from the group consisting of the following: a substituted or unsubstituted (C5-C30) arylene group, and a substituted or unsubstituted (C5-C30) heteroarylene group, and $Ar_2$ is selected from the group consisting of the following: a substituted or unsubstituted (C5-C30) aryl group, a substituted or unsubstituted (C5-C30) aryloxy group, and a substituted or unsubstituted (C4-C30) heteroaryl group.

m is an integer from 0 to 5, and

—$(Ar_1)_m$— groups in —$(Ar_1)_m$—$(Ar_2)$ are identical or different from one another;

and with the proviso that at least one of R1, R2, R3, and R4 comprises at least 10 carbon atoms and one cyclic aromatic ring;

and with the proviso that none of R1, R2, R3, R4, R5, R6, R7, R8, R9 and R10 comprise a hydroxyl, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and for Formula B1, R2, R3, R4, R5, R6, R7, R8, R9, R10, R2a, R3a, R4a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and with the proviso that none of R2, R3, R4, R5, R6, R7, R8, R9, R10, R2a, R3a, R4a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom; and for Formula B2, R1, R3, R4, R5, R6, R7, R8, R9, R10, R1a, R3a, R4a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and with the proviso that none of R1, R3, R4, R5, R6, R7, R8, R9, R10, R1a, R3a, R4a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom; and for Formula B3, R1, R2, R4, R5, R6, R7, R8, R9, R10, R1a, R2a, R4a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and with the proviso that none of R1, R2, R4, R5, R6, R7, R8, R9, R10, R1a, R2a, R4a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom; and for Formula B4, R1, R2, R3, R5, R6, R7, R8, R9, R10, R1a, R2a, R3a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and with the proviso that none of R1, R2, R3, R5, R6, R7, R8, R9, R10, R1a, R2a, R3a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom.

In one embodiment, the at least one compound is selected from Formula A or Formula B3.

In one embodiment, at least one compound is selected from Formula A. In a further embodiment, for Formula A, each of R5, R6, R7, R8, R9 and R10 is hydrogen.

In one embodiment, for Formula A, each of R1, R2 and R4 are hydrogen.

In one embodiment, for Formula A, each of R5, R6, R7, R8, R9 and R10 is hydrogen, and wherein at least one of R1, R2, R3 or R4 comprises at least 12 carbon atoms. In a further embodiment, R3 comprises at least 12 carbon atoms.

In one embodiment, for Formula A, each of R1, R2, R3, R4, R5, R6, R7, R8, R9 and R10 is, independently, hydrogen or —(Ar$_1$)$_m$—(Ar$_2$), as defined above, wherein each Ar$_1$ is, independently from one another, selected from the group consisting of a phenylene group, a (C1-C10 alkyl)phenylene group, a naphthylene group, a (C1-C10 alkyl) naphthylene group, a fluorenylene group, a (C1-C10 alkyl)fluorenylene group, a di(C1-C10 alkyl)fluorenylene group, a phenanthrylene group, a (C1-C10 alkyl)phenanthrylene group, a di(C1-C10 alkyl)phenanthrylene group; with the proviso that at least one of R1, R2, R3, R4, R5, R6, R7, R8, or R9 is not hydrogen.

In one embodiment, for Formula A, each of R1, R2, R3, R4, R5, R6, R7, R8, R9 and R10 is, independently, hydrogen or —(Ar$_1$)$_m$—(Ar$_2$), as defined above, wherein Ar$_2$ is selected from the group consisting of a phenyl group, a (C1-C10 alkyl)phenyl group, a di(C1-C10 alkyl)phenyl group, a (C6-C14 aryl)phenyl group, a di(C6-C14 aryl)phenyl group, a naphthyl group, a (C1-C10 alkyl)naphthyl group, a di(C1-C10 alkyl)naphthyl group, a (C6-C14 aryl) naphthyl group, a di(C6-C14 aryl)naphthyl group, an anthryl group, a (C1-C10 alkyl) anthryl group, a di(C1-C10 alkyl)anthryl group, a (C6-C14 aryl) anthryl group, a di(C6-C14 aryl)anthryl group, a tetra(C1-C10 alkyl)-9,10-dihydroanthracenyl group, a phenanthryl group, a (C1-C10 alkyl) phenanthryl group, a di(C1-C10 alkyl)phenanthryl group, a (C6-C14) aryl phenanthryl group, a di(C6-C14 aryl)phenanthryl group, a fluorenyl group, a C1-C10 alkyl fluorenyl group, a di(C1-C10 alkyl) fluorenyl group, a (C6-C14 aryl) fluorenyl group, a di(C6-C14 aryl) fluorenyl group, a pyridyl group, a (C1-C10 alkyl) pyridyl group, a di(C1-C10 alkyl)pyridyl group, a pyrenyl group, a (C1-C10 alkyl) pyrenyl group, a di(C1-C10 alkyl) pyrenyl group, a (C6-C14 aryl) pyrenyl group, a di(C6-C14 aryl)pyrenyl group, a phenanthrolinyl group, a (C1-C10 alkyl) phenanthrolinyl group, a di(C1-C10 alkyl)phenanthrolinyl group, a (C6-C14 aryl) phenanthrolinyl group, a di(C6-C14 aryl) phenanthrolinyl group, a benzimidazolyl group, a (C1-C10 alkyl) benzimidazolyl group, a di(C1-C10 alkyl)benzimidazolyl group, a (C6-C14 aryl) benzimidazolyl group, a di(C6-C14 aryl)benzimidazolyl group, an imidazolpyridinyl group, a (C1-C10 alkyl) imidazolpyridinyl group, a di(C1-C10 alkyl)imidazolpyridinyl group, a (C6-C14 aryl) imidazolpyridinyl group, a di(C6-C14 aryl)imidazolpyridinyl group, an imidazolpyrimidinyl group, a (C1-C10 alkyl) imidazolpyrimidinyl group, a di(C1-C10 alkyl) imidazolpyrimidinyl group, a (C6-C14 aryl) imidazolpyrimidinyl group, a di(C6-C14 aryl)imidazolpyrimidinyl group, a carbazolyl group, a (C1-C10 alkyl) carbazolyl group, a di(C1-C10 alkyl) carbazolyl group, a (C6-C14 aryl) carbazolyl group, a di(C6-C14 aryl)carbazolyl group, a di(C1-C10)alkyl-9H-indeno[2,1-c]pyridine group, a di(C6-C14 aryl)-1,3,5-triazinyl group, a tetra(C1-C10)alkyl-6,12-dihydroindeno[1,2-b]fluorenyl group, an imidazolpyrimidinyl group, a di(C1-C10)alkyl-9H-xanthenyl group, a benzofuranyl group, a dibenzo[b,d]furanyl group; with the proviso that at least one of R1, R2, R3, R4, R5, R6, R7, R8, or R9 is not hydrogen. In a further embodiment, for Formula A, each of R5, R6, R7, R8, R9 and R10 is hydrogen.

In one embodiment, for Formula A, R1, R2, R3, R4, R5, R6, R7, R8, R9, and R10 are each, independently, hydrogen or selected from the following group of substituents:

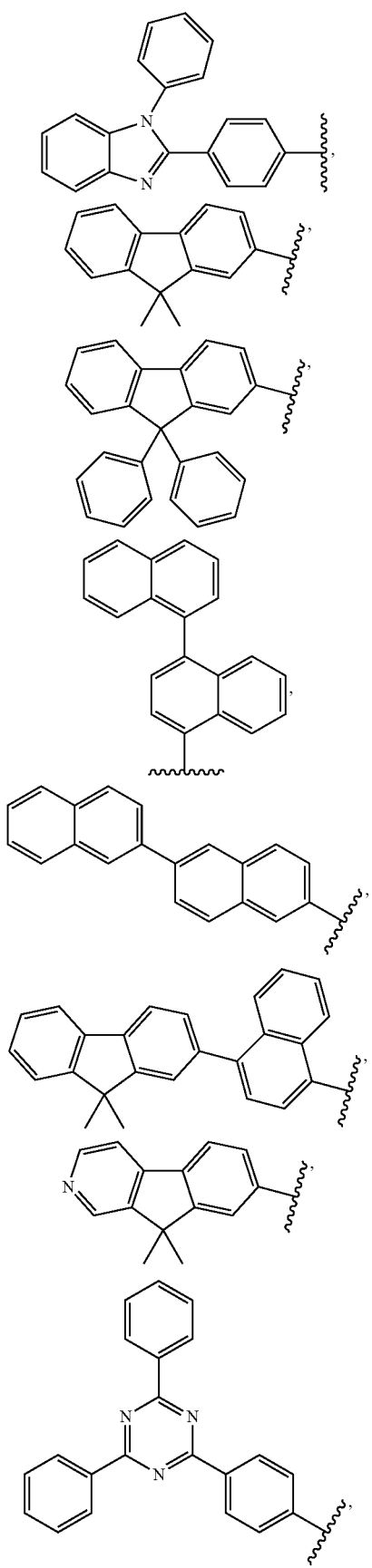
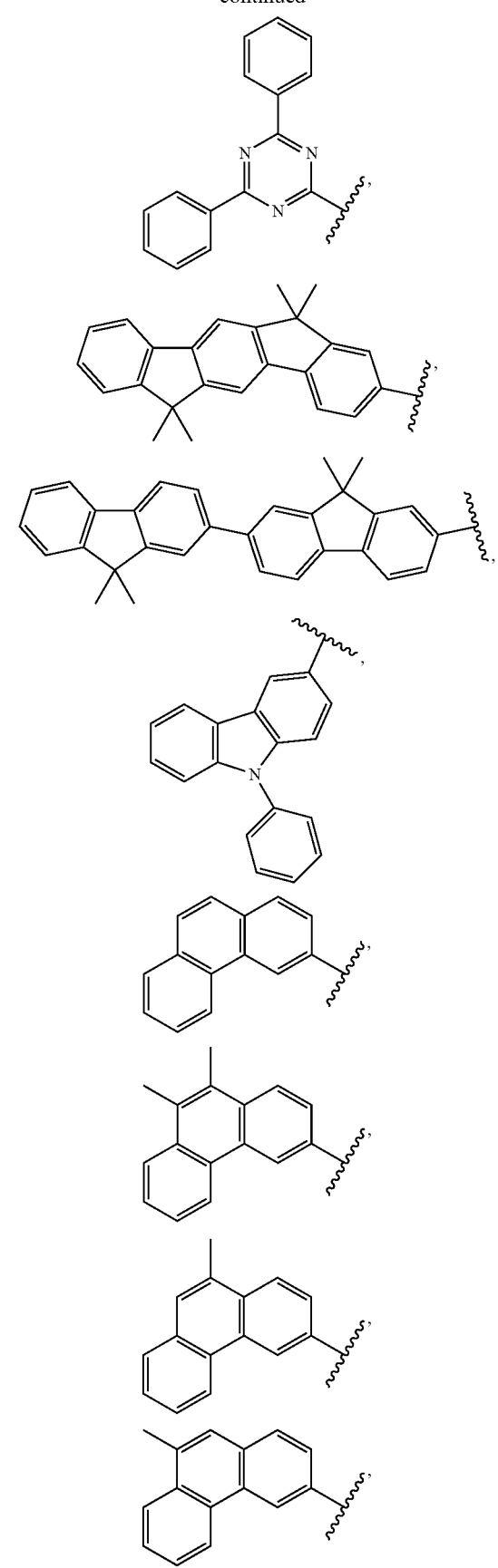

-continued

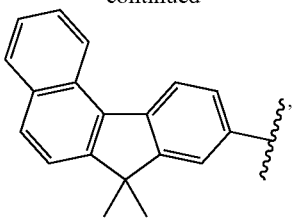

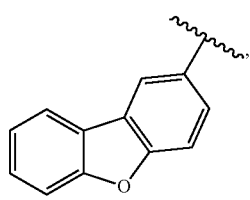

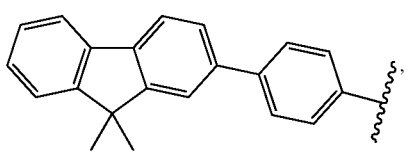

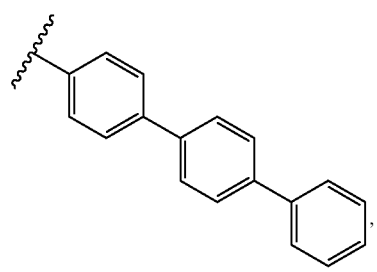

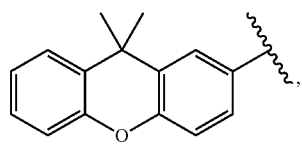

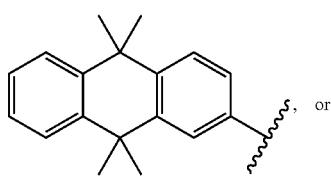, or

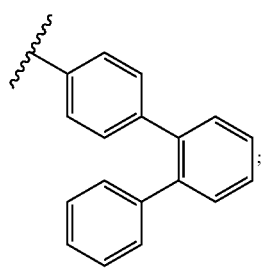;

wherein the external connection point of each substituent is indicated by a wavy line, as recommended by current IUPAC standards: *Pure Appl. Chem.*, 2008, 80, 277 (*Graphical representation standards for chemical structural diagrams*), and with the proviso that at least one of R1, R2, R3, R4, R5, R6, R7, R8, R9 and R10 is not hydrogen. In a further embodiment, R5, R6, R7, R8, R9 and R10 are each hydrogen. In a further embodiment, R1 and R4 are each hydrogen. In a further embodiment, R2 is hydrogen.

In one embodiment, the compound of Formula A is selected from the following:

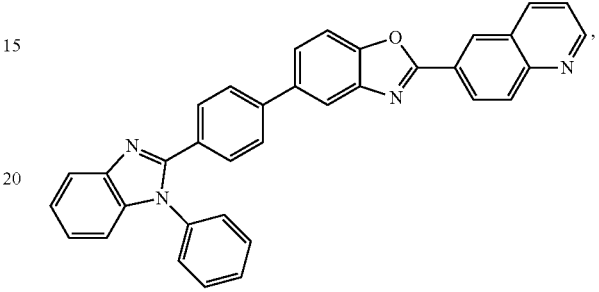,

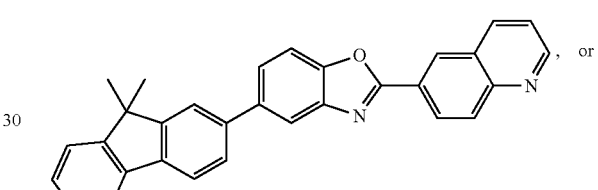, or

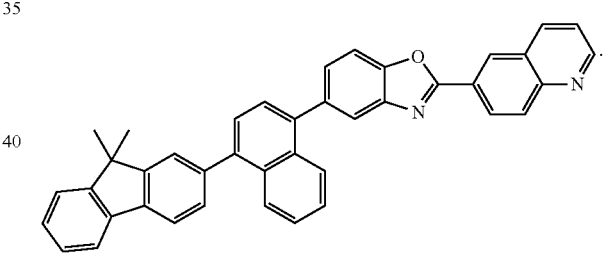.

The compound of Formula A may comprise a combination of two or more embodiments as described herein.

In one embodiment, the at least one compound is selected from Formula B3.

In one embodiment, for Formula B3, L comprises at least two carbon atoms.

In one embodiment, for Formula B3, L is a cyclic structure comprising at least 5 atoms.

In one embodiment, for Formula B3, L comprises at least one C=C double bond or at least one C=O double bond.

In one embodiment, for Formula B3, R1, R2, R4, R5, R6, R7, R8, R9 and R10 are each hydrogen. In a further embodiment, R1a, R2a, R4a, R6a, R6a, R7a, R8a, R9a and R10a are each hydrogen.

In one embodiment, for the compound of Formula B3 is selected from the following:

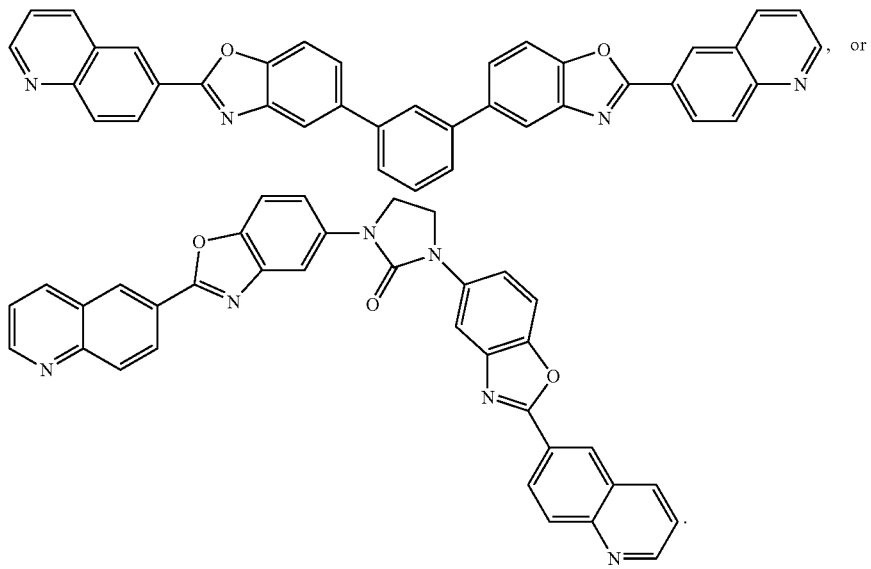

The compound of Formula B3 may comprise a combination of two or more embodiments as described herein.

In one embodiment, the at least one compound is selected from Formula B1.

In one embodiment, for Formula B1, L comprises at least two carbon atoms.

In one embodiment, for Formula B1, L is a cyclic structure comprising at least 5 atoms.

In one embodiment, for Formula B1, L comprises at least one C=C double bond or at least one C=O double bond.

The compound of Formula B1 may comprise a combination of two or more embodiments as described herein.

In one embodiment, the at least one compound is selected from Formula B2.

In one embodiment, for Formula B2, L comprises at least two carbon atoms.

In one embodiment, for Formula B2, L is a cyclic structure comprising at least 5 atoms.

In one embodiment, for Formula B2, L comprises at least one C=C double bond or at least one C=O double bond.

The compound of Formula B2 may comprise a combination of two or more embodiments as described herein.

In one embodiment, the at least one compound is selected from Formula B4.

In one embodiment, for Formula B4, L comprises at least two carbon atoms.

In one embodiment, for Formula B4, L is a cyclic structure comprising at least 5 atoms.

In one embodiment, for Formula B4, L comprises at least one C=C double bond or at least one C=O double bond.

The compound of Formula B4 may comprise a combination of two or more embodiments as described herein.

In one embodiment, the at least one compound (of Formula A, B1, B2, B3 or B4) has a CLogP value greater than 6.4, as determined by the "Chemical Properties" calculation, as implemented in the "CLogP" function ChemBioDraw Ultra, Version 12.0.2.1076, CambridgeSoft 2010. Log P is the partition coefficient, and is a measure of the hydrophilicity of a compound. CLogP is a common predictive computational method to predict Log P. In a further embodiment, the at least one compound (of Formula A, B1, B2, B3 or B4) has a CLogP value greater than 6.8, further greater than 7.0, further greater than 7.2, or further greater than 7.4.

In one embodiment, the at least one compound (of Formula A, B1, B2, B3 or B4) has a molecular weight greater than, or equal to, 400 g/mole, further greater than, or equal to, 450 g/mole.

In one embodiment, the at least one compound (of Formula A, B1, B2, B3 or B4) has a HOMO level from −7.0 eV to −5.0 eV, further from −6.5 eV to −5.0 eV, further from −6.0 eV to −5.0 eV.

In one embodiment, the at least one compound (of Formula A, B1, B2, B3 or B4) has a LUMO level from −1.6 eV to −2.2 eV, further from −1.7 eV to −2.2 eV, further from −1.8 eV to −2.2 eV.

In one embodiment, the at least one compound (of Formula A, B1, B2, B3 or B4) has a Triplet Energy level from 1.9 eV to 4.0 eV, further from 2.0 eV to 3.5 eV, further from 2.1 eV to 3.0 eV.

In one embodiment, the at least one compound (of Formula A, B1, B2, B3 or B4) has a sublimation temperature greater than, or equal to 200° C.

An inventive compound (of Formula A, B1, B2, B3 or B4) may comprise a combination of two or more embodiments as described herein.

In one embodiment, the composition further comprises a metal quinolate. In a further embodiment, the metal quinolate is lithium quinolate.

In one embodiment, the composition comprises from 10 to 90 weight percent of the metal quinolate, based on the weight of the composition. In a further embodiment, the composition comprises from 10 to 50 weight percent of the metal quinolate, based on the weight of the composition. In a further embodiment, the composition comprises from 20 to 50 weight percent of the metal quinolate, based on the weight of the composition.

In one embodiment, the composition comprises from 10 to 90 weight percent of the lithium quinolate, based on the weight of the composition. In a further embodiment, the composition comprises from 10 to 50 weight percent of the lithium quinolate, based on the weight of the composition. In a further embodiment, the composition comprises from 20 to 50 weight percent of the lithium quinolate, based on the weight of the composition.

An inventive composition may comprise a combination of two or more embodiments as described herein.

The invention also provides a film comprising at least one layer formed from an inventive composition of one or more embodiments described herein.

The invention also provides an electronic device comprising at least one film layer formed from an inventive composition of one or more embodiments described herein.

The invention also provides an electronic device comprising at least one component formed from an inventive composition of one or more embodiments described herein.

The inventive compositions are useful for application in organic light emitting diodes (OLED) or related organic electronic devices, including organic solar cells. More specifically, the invented compositions find application in individual layers of OLEDs, including HIL (hole injection layers), HTL (hole transport layers), EML (emissive layers, including host and dopant), ETL (electron transport layers).

An inventive film may comprise a combination of two or more embodiments as described herein.

An inventive device may comprise a combination of two or more embodiments as described herein.

The term "aryl," used herein, represents an organic radical derived from aromatic hydrocarbon. An aryl group may be a monocyclic and/or fused ring system, each ring of which may suitably contain from 4 to 7, preferably from 5 or 6 cyclic atoms. Structures wherein two or more aryl groups are combined through single bond(s) are also included. Specific examples include phenyl, naphthyl, biphenyl, anthryl, indenyl, fluorenyl, phenanthryl, triphenylenyl, pyrenyl, perylenyl, chrysenyl, naphtacenyl, fluoranthenyl and the like, but are not restricted thereto. The naphthyl may be 1-naphthyl or 2-naphthyl, the anthryl may be 1-anthryl, 2-anthryl or 9-anthryl, and the fluorenyl may be any one of 1-fluorenyl, 2-fluorenyl, 3-fluorenyl, 4-fluorenyl or 9-fluorenyl.

The term "heteroaryl," used herein, means an aryl group containing at least one heteroatom selected from, for example, B, N, O, S, P(=O), Si and P. The heteroaryl may be a 5- or 6-membered monocyclic heteroaryl or a polycyclic heteroaryl, which is fused with one or more benzene ring(s), and may be partially saturated. The structures having one or more heteroaryl group(s) bonded through a single bond are also included. The heteroaryl groups may include divalent aryl groups, of which the heteroatoms are oxidized or quarternized to form N-oxides, quaternary salts, or the like. Specific examples include, but are not limited to, monocyclic heteroaryl groups, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; polycyclic heteroaryl groups, such as benzofuranyl, benzothiophenyl, isobenzofuranyl, benzimidazolyl, benzothiazolyl, benzisothiazolyl, benzisoxazolyl, benzoxazolyl, isoindolyl, indolyl, indazolyl, benzothia-diazolyl, quinolyl, isoquinolyl, cinnolinyl, quinazolinyl, quinoxalinyl, carbazolyl, phenanthridinyl and benzodioxolyl; and corresponding N-oxides (for example, pyridyl N-oxide, quinolyl N-oxide) and quaternary salts thereof.

Some examples of substituents include the following: deuterium, halogen, (C1-C30)alkyl with or without halogen substituent(s), (C6-C30)aryl, (C3-C30)heteroaryl with or without (C6-C30)aryl substituent(s), a 5- to 7-membered heterocycloalkyl containing one or more heteroatom(s) selected from, for example, B, N, O, S, P(=O), Si and P, a 5- to 7-membered heterocycloalkyl fused with one or more aromatic ring(s), (C3-C30)cycloalkyl, (C6-C30)cycloalkyl fused with one or more aromatic ring(s), tri(C1-C30)alkylsilyl, di(C1-C30)alkyl(C6-C30)arylsilyl, tri(C6-C30)arylsilyl, adamantyl, (C7-C30)bicycloalkyl, (C2-C30)alkenyl, (C2-C30)alkynyl, cyano, carbazolyl, $NR_2iR_{22}$, $BR_{23}R_{24}$, $PR_{25}R_{26}$, $P(=O)R_{27}R_{28}$ [wherein $R_2i$ through $R_{28}$ independently represent (C1-C30)alkyl, (C6-C30)aryl or (C3-C30)heteroaryl], (C6-C30)ar(C1-C30)alkyl, (C1-C30)alkyl(C6-C30)aryl, (C1-C30)alkyloxy, (C1-C30)alkylthio, (C6-C30)aryloxy, (C6-C30)arylthio, (C1-C30)alkoxycarbonyl, (C1-C30)alkylcarbonyl, (C6-C30)arylcarbonyl, (C6-C30)aryloxycarbonyl, (C1-C30)alkoxycarbonyloxy, (C1-C30)alkylcarbonyloxy, (C6-C30)arylcarbonyloxy, (C6-C30)aryloxycarbonyloxy, carboxyl, nitro and hydroxyl; or that the adjacent substituents are linked together to form a ring.

EXPERIMENTAL

Reagents and Test Methods

All solvents and reagents were obtained from commercial vendors including Sigma-Aldrich, Fisher Scientific, Acros, TCI and Alfa Aesar, were used in the highest available purities, and/or were, when necessary, recrystallized before use. Dry solvents were obtained from in-house purification/dispensing system (hexane, toluene, tetrahydrofuran and diethyl ether), or purchased from Sigma-Aldrich. All experiments involving water sensitive compounds were conducted in "oven dried" glassware, under nitrogen atmosphere, or in a glovebox. Reactions were monitored by analytical thin-layer chromatography (TLC) on precoated aluminum plates (VWR 60 F254), visualized by UV light and/or potassium permanganate staining. Flash chromatography was performed on an ISCO COMBIFLASH system with GRACERESOLV cartridges.

$^1$H-NMR-spectra (500 MHz or 400 MHz) were obtained on a Varian VNMRS-500 or VNMRS-400 spectrometer at 30° C., unless otherwise noted. The chemical shifts were referenced, depending on the NMR solvent used, to one of the following: TMS in $CHCl_3$ ($\delta$=0.00) in CDCl3, Benzene-$d_5$ (7.15) in Benzene-$d_6$ or DMSO-$d_5$ ($\delta$ 2.50) in DMSO-$d_6$. If necessary, peak assignment was carried out with the help of COSY, HSQC or NOESY experiments to confirm structural identity.

$^{13}$C-NMR spectra (125 MHz or 100 MHz) were obtained on a Varian VNMRS-500 or VNRMS-400 spectrometer, and referenced, depending on the NMR solvent used, to solvent or standard signals (0.0—TMS in $CDCl_3$, 128.02—Benzene-$d_6$, 39.43—DMSO-$d_6$).

Routine LC/MS studies were carried out as follows. Five microliter aliquots of the sample, as "3 mg/ml solution in THF," were injected on an AGILENT 1200SL binary gradient liquid chromatography, coupled to an AGILENT 6520 QT of, quadrupole-time of flight MS system, via a dual spray electrospray (ESI) interface operating in the PI mode. The following analysis conditions were used: column: 150×4.6 mm ID, 3.5 μm ZORBAX SB-C8; column temperature: 40° C.; mobile phase: 75/25 A/B to 15/85 A/B at 40 minutes; solvent A=0.1v % formic acid in water; solvent B=THF; flow-1.0 mL/min; UV detection: diode array 210 to 600 nm (extracted wavelength 250,280 nm); ESI conditions: gas temperature 365° C.; gas flow—8 ml/min; capillary—3.5 kV; nebulizer—40 PSI; fragmentor—145V.

All computations (orbital energies, etc.) utilized the Gaussian-09 program[1]. The calculations were performed with the hybrid density functional theory (DFT) method, B3LYP,[2] and the 6-31G*(5d) basis set.[3] The singlet state calculations used the closed shell approximation, and the triplet state calculations used the open shell approximation. All values are quoted in electronvolts (eV). The HOMO and LUMO values were determined from the orbital energies of the optimized geometry of the singlet ground state. The triplet energies were determined as the difference between the total energy of the optimized triplet state and the optimized singlet state.

See also the following:
1. Gaussian 09, Revision A.02, Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, N.; Vreven, T.; Montgomery, Jr., J. A.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, J. M.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, O.; Foresman, J. B.; Ortiz, J. V.; Cioslowski, J.; Fox, D. J., Gaussian, Inc., Wallingford Conn., 2009.
2. (a) Becke, A. D. *J. Chem. Phys.* 1993, 98, 5648. (b) Lee, C.; Yang, W.; Parr, R. G. *Phys. Rev B* 1988, 37, 785. (c) Miehlich, B.; Savin, A.; Stoll, H.; Preuss, H. *Chem. Phys. Lett.* 1989, 157, 200.
3. (a) Ditchfield, R.; Hehre, W. J.; Pople, J. A. *J. Chem. Phys.* 1971, 54, 724. (b) Hehre, W. J.; Ditchfield, R.; Pople, J. A. *J. Chem. Phys.* 1972, 56, 2257. (c) Gordon, M. S. *Chem. Phys. Lett.* 1980, 76, 163.

Individual Reactions

Quinoline-6-carbonyl chloride (Precursor I)

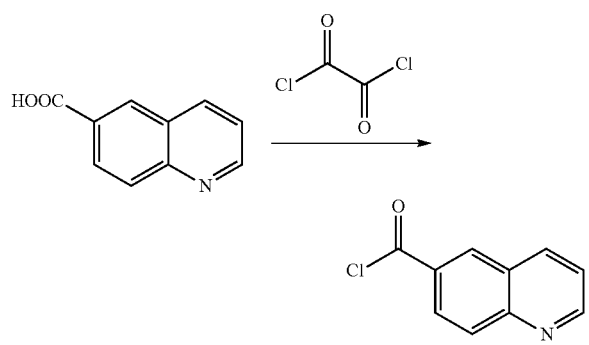

Under nitrogen, a 1 L round bottom flask, equipped with septum and drying tube attached to a gas scrubber setup, was charged with 25.4 g (146.5 mmol) quinoline-6-carboylic acid. 1,4-Dioxane (250 mL) was added along with 10 drops of DMF. Inside a glovebox, oxalyl chloride (25.1 g, 197.8 mmol, 1.35 eq) was weighed into a septum vial. The vial was closed, removed from the glovebox, and the weighed oxalyl chloride was added, under nitrogen, to the reaction, in portions, via syringe. The reaction was stirred until most of the gas development ceased. The reaction remained stirring at room temperature overnight. The volatiles were removed using a rotary evaporator. Trace HCl was removed by addition of several aliquots of dry toluene, which were consecutively evaporated using the rotary evaporator. The final product was obtained in form of a colorless to slightly yellow powder (28.0 g, 146.4 mmol, 100%). $^{1}$H-NMR: (500 MHz, CDCl3) δ 9.35 (dd, J=5.2, 1.5 Hz, 1H), 9.09 (d, J=8.5 Hz, 1H), 9.09 (d, J=9.0 Hz, 1H), 9.01 (d, J=2.0 Hz, 1H), 8.64 (dd, J=9.1, 2.0 Hz, 1H), 8.14 (dd, J=8.4, 5.2 Hz, 1H); $^{13}$C-NMR (126 MHz, CDCl$_3$) δ 122.92, 123.90, 128.21, 133.44, 133.79, 134.55, 140.95, 146.44, 147.11, 166.69.

N-(2,5-Dibromophenyl)quinoline-6-carboxamide (Precursor 2)

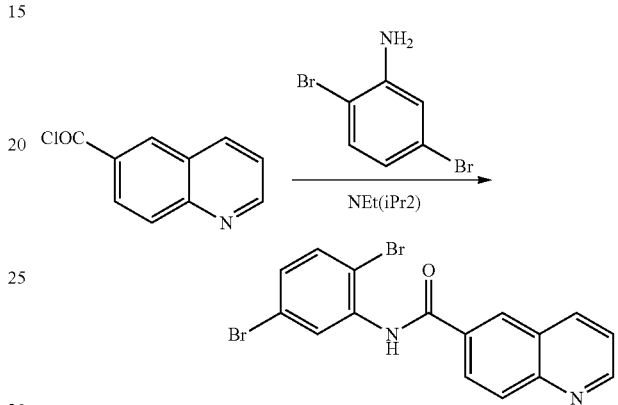

2,5-Dibromaniline was recrystallized from a toluene/hexane solvent mixture. Under nitrogen, in a 1 L, single-necked round bottom flask, with larger stir bar and reflux condenser, 2,6-dibromoaniline (36.1 g, 144 mmol) and quinoline-6-carbonyl chloride (Precursor 1, 27.3 g, 142 mmol, 0.99 eq) were dissolved in dry 1,4-dioxane (350 mL). Hünig's base (37.2 g, 288 mmol, 2.0 eq) was added while stirring. The content of the flask was heated to approximately 40° C. by the reaction exotherm. The mixture was stirred, and allowed to cool back to room temperature. The reaction was heated to 100° C., in an oil bath, for 20 hours. A TLC was taken, showing complete consumption of 2,5-dibromoaniline. The reaction mixture was poured hot into 1.5 L of water, upon which a fine precipitate formed. The solution was basified with sodium carbonate and filtered. The collected residue was dried by suction, and washed with acetone (25 mL) and toluene (25 mL). The filter cake was transferred to a 1 L flask, and trace water was removed by azeotropic distillation with toluene on the rotary evaporator, followed by application of high vacuum overnight. The dried residue was recrystallized from monochlorobenzene (1.5 L), using activated charcoal as a decolorizing agent. The crystals were isolated by filtration, and dried under high vacuum (45.05 g, 111 mol, 77.1%, off-white needles). Further purification was achieved by recrystallization from 1,4-dioxane (~0.9 L). The final product (40.0 g, 98.5 mmol, 68.5%) was obtained in form of off-white crystals (platelets). $^1$H NMR (500 MHz, DMSO-d$_6$) δ 10.38 (s, 1H), 9.03 (dd, J=4.2, 1.7 Hz, 1H), 8.68 (d, J=2.0 Hz, 1H), 8.55 (ddd, J=8.3, 1.6, 0.8 Hz, 1H), 8.28 (dd, J=8.8, 2.0 Hz, 1H), 8.16 (d, J=8.8 Hz, 1H), 7.87 (d, J=2.4 Hz, 1H), 7.71 (d, J=8.6 Hz, 1H), 7.65 (dd, J=8.3, 4.2 Hz, 1H), 7.46 (dd, J=8.6, 2.4 Hz, 1H); $^{13}$C-NMR (126 MHz, DMSO-d$_6$) δ 119.73, 120.70, 122.78, 127.59, 128.26, 129.19, 129.77, 131.01, 131.25, 132.09, 134.78, 137.63, 138.58, 149.45, 152.86, 165.52. GC/CI⁺ m/z (%): 404.96 (50) [M+H, 2×$^{79}$Br]⁺, 406.97 (100) [M+H, $^{79}$Br, $^{81}$Br]⁺, 408.96 (50) [M+H, 2×$^{81}$Br]⁺.

5-Bromo-2-(quinolin-6-yl)benzo[d]oxazole (Precursor 3)

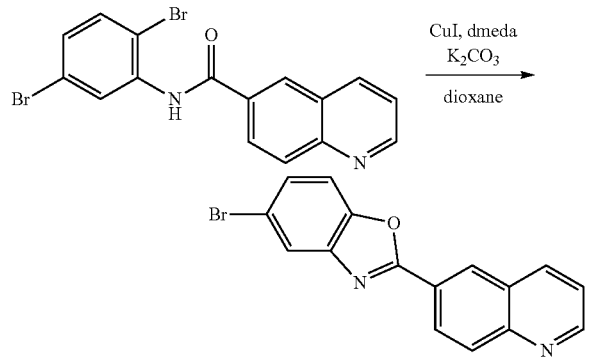

All reaction steps were performed inside a glove box. Copper iodide (821 mg, 4.31 mmol, 0.05 eq) was dissolved in 1,4-dioxane (8 mL), and N,N'-dimethylethylene-diamine (928 μL, 760 mg, 8.62 mmol, 0.1 eq) was added. Precursor 2 (35.0 g, 86.2 mmol, 1.0 eq) was weighed into a separate 1 L flask. Tripotassium phosphate (54.9 g, 259 mmol, 3.0 eq) was finely ground with a mortar (inside the glove box), and was added to the flask, along with 300 mL of 1,4-dioxane. The reaction was started by addition of the copper iodine/N,N'-dimethylethylenediamine solution, stirred vigorously, and heated to 90° C. over night. The product was precipitated by pouring the contents of the reaction vessel into diluted aqueous ammonium hydroxide. The precipitate was isolated by filtration, and washed with water, followed by a small amount of acetone, and dried under high vacuum. The dried precipitate was dissolved in chloroform, and filtered through a short plug of silica and basic alumina. The eluent was collected, and the solvent was removed by rotary evaporation. The residue was dissolved in a minimal amount of boiling ethyl acetate (approximately one liter). Gradual cooling in a Dewar container, resulted in the crystallization of the pure benzoxazole in form of colorless microcrystals. The product was isolated by filtration and dried under high vacuum (17.0 g, 52.3 mmol, 60.7%). ¹H-NMR (500 MHz, CDCl₃) δ 9.00 (dd, J=4.2, 1.7 Hz, 1H), 8.71 (d, J=1.9 Hz, 1H), 8.51 (dd, J=8.9, 2.0 Hz, 1H), 8.31-8.24 (m, 1H), 8.23 (d, J=8.8 Hz, 1H), 7.93 (t, J=1.2 Hz, 1H), 7.53-7.45 (m, 3H); ¹³C-NMR (126 MHz, CDCl₃) δ 111.84, 117.55, 122.13, 123.17, 124.67, 127.57, 127.95, 128.19, 128.44, 130.56, 136.81, 143.74, 149.58, 149.91, 152.18, 163.47; GC/ESE m/z (%): 326.03 (100) [M+H, $^{79}$Br]⁺, 328.03 (100) [M+H, $^{81}$Br]⁺.

5-(9,9-Dimethyl-9H-fluoren-2-yl)-2-(quinolin-6-yl)benzo[d]oxazole (Compound 1)

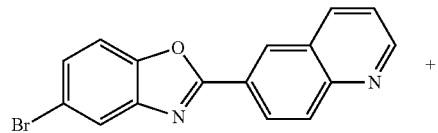

+

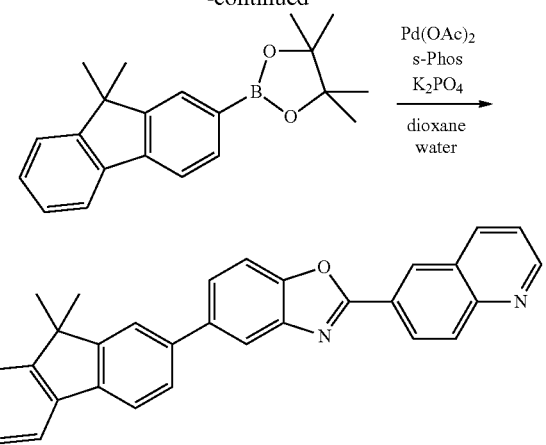

Inside a glove box, Pd(OAc)₂ (20.7 mg, 92 μmol, 0.005 eq) and s-Phos [2-dicyclohexylphosphino-2',6'-dimethoxybiphenyl, available from Aldrich] (75.8 mg, 185 μmol, 0.01 eq) were dissolved in 2.5 mL of 1,4-dioxane. Tripotassium phosphate (11.8 g, 55.4 mmol, 3 eq) was weighed into a 250 mL round bottom flask, and 12 mL of water was added. 5-Bromo-2-(quinolin-6-yl)benzo[d]oxazole (Precursor 3, 6.00 g, 18.5 mmol) and 2-(9,9-dimethyl-9H-fluoren-2-yl)-4,4,5,5-tetramethyl-1,3,2-dioxaborolane (available from Alpha Aesar, 7.09 g, 22.14 mmol, 1.2 eq) were dissolved in 1,4-dioxane (75 mL), and added to the tripotassium phosphate/water slurry. While stirring, the catalyst solution was added to the reaction, which continued to stir at room temperature over night. The reaction was then diluted with approximately 300 mL chloroform, and filtered through a plug of basic alumina and silica. Flash column purification (0-2% methanol in chloroform) resulted in clean separation of the product. After removal of the solvent, via rotary evaporation, the residue was recrystallized from inhibitor-free 1,4-dioxane.

The product was obtained in form of colorless needles, which were isolated by filtration, and washed with a small amount of 1,4-dioxane (4.15 g, 9.46 mmol, 51.3%, organic purity: 100.0% according to LC/MS). A second batch of crystals was obtained by from the mother liquor by concentration at high temperature, followed by slow cooling to room temperature over night (1.94 g, 4.41 mmol, 23.9%, organic purity: 99.8%). The combined yield of this reaction was 75.2%. ¹H-NMR (500 MHz, CDCl₃) δ 8.99 (dd, J=4.2, 1.7 Hz, 1H), 8.75 (d, J=1.9 Hz, 1H), 8.58 (dd, J=8.8, 1.9 Hz, 1H), 8.28 (dt, J=8.3, 1.1 Hz, 1H), 8.25 (d, J=8.8 Hz, 1H), 8.07 (t, J=1.2 Hz, 1H), 7.81 (d, J=7.8 Hz, 1H), 7.77-7.73 (m, 1H), 7.70 (d, J=1.6 Hz, 1H), 7.67 (s, 2H), 7.62 (dd, J=7.8, 1.7 Hz, 1H), 7.49-7.44 (m, 2H), 7.35 (pd, J=7.4, 1.4 Hz, 2H), 1.56 (s, 6H); ¹³C NMR (126 MHz, CDCl₃) δ 27.25, 67.08, 110.63, 118.57, 120.10, 120.38, 121.68, 122.06, 122.62, 125.15, 126.45, 127.05, 127.33, 127.66, 127.90, 128.00, 130.47, 136.82, 138.55, 138.73, 139.07, 140.01, 142.81, 149.47, 150.41, 152.00, 153.84, 154.38, 162.94; ESI/LC/MS/MS: m/z=439 (base peak, [M+H]⁺), fragmenting into 423, 241, 239, 129, 155, 268. CLogP: 8.259 (ChemBioDraw Ultra, Version 12.0.2.1076, CambridgeSoft 2010). Additional computed data: HOMO: −5.56 eV, LUMO: −1.91 eV, Triplet Energy: 2.42 eV.

5-(4-(1-Phenyl-1H-benzo[d]imidazol-2-yl)phenyl)-2-(quinolin-6-yl)benzo[d]oxazole (Compound 2)

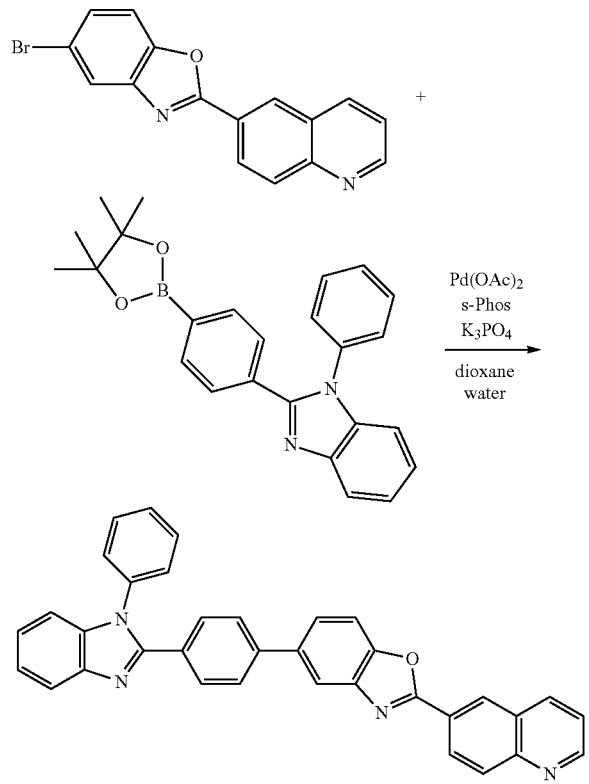

Inside a glove box, Pd(OAc)$_2$ (19.0 mg, 85 µmol) and s-Phos [2-dicyclohexylphosphino-2',6'-dimethoxybiphenyl, available from Aldrich] (69.4 mg, 169 µmol) were dissolved in 1,4-dioxane (1 mL). Tripotassium phosphate (10.8 g, 50.7 mmol, 3 eq) was weighed into a 20 mL vial, and 10.6 mL of degassed water was added. 5-Bromo-2-(quinolin-6-yl)benzo[d]oxazole ((Precursor 3, 5.50 g, 16.9 mmol) and 1-phenyl-2-(4-(4,4,5,5-tetramethyl-1,3,2-dioxaborolan-2-yl)phenyl)-1H-benzo[d]imidazole (7.04 g, 17.8 mmol, 1.05 eq; the synthesis of this boronic ester is known in the art, e.g., US20100326526A1)) were dissolved in 70 mL 1,4-dioxane, and the aqueous tripotassium phosphate solution was added, followed by the catalyst solution. The mixture was stirred at room temperature overnight.

The reaction was worked up by adding chloroform and water, until both phases appeared clear. The chloroform phase was separated, the aqueous phase re-extracted with chloroform, and the combined organic phases were dried over magnesium sulfate. The mixture was filtered through a short plug of basic alumina and activated charcoal, and adsorbed to silica by rotary evaporation of the solvent. The powder was loaded on top of a plug of basic alumina in an ISCO dryloading cartridge. The compound was purified by column chromatography using a 350 g Grace normal phase silica cartridge and 1% MeOH in chloroform, isocratic gradient. The TLC-pure fractions were combined, and the solvent removed by rotary evaporation. Addition of hot toluene to the residue resulted in delayed crystallization. The fine crystals were isolated by filtration and dried at 50° C. under high vacuum overnight. $^1$H-NMR (500 MHz, CDCl$_3$) δ 8.99 (dd, J=4.2, 1.7 Hz, 1H), 8.74 (d, J=1.9 Hz, 1H), 8.55 (dd, J=8.8, 1.9 Hz, 1H), 8.28 (ddd, J=8.6, 1.6, 0.7 Hz, 1H), 8.24 (dd, J=8.8, 0.7 Hz, 1H), 7.98 (dd, J=1.7, 0.7 Hz, 1H), 7.92 (dt, J=8.1, 0.9 Hz, 1H), 7.74-7.44 (m, 10H), 7.40-7.32 (m, 3H), 7.30-7.22 (m, 2H); $^{13}$C-NMR (126 MHz, CDCl$_3$) δ 110.45, 110.78, 118.56, 119.86, 122.09, 123.04, 123.39, 124.97, 125.04, 127.19, 127.50, 127.65, 127.98, 128.00, 128.68, 128.92, 129.92, 129.97, 130.49, 136.84, 137.07, 137.38, 137.57, 141.72, 142.85, 143.08, 149.49, 150.72, 151.94, 152.06, 163.08; ESI/LC/MS/MS: m/z=515 (base peak, [M+H]$^+$), fragmenting into 167, 332, 515. CLogP: 8.918 (ChemBioDraw Ultra, Version 12.0.2.1076, CambridgeSoft 2010). Additional computed data: HOMO: −5.59 eV, LUMO: −1.94 eV, Triplet Energy: 2.47 eV.

5-(4-(9,9-Dimethyl-9H-fluoren-3-yl)naphthalen-1-yl)-2-(quinolin-6-yl)benzo[d]oxazole (Compound 3)

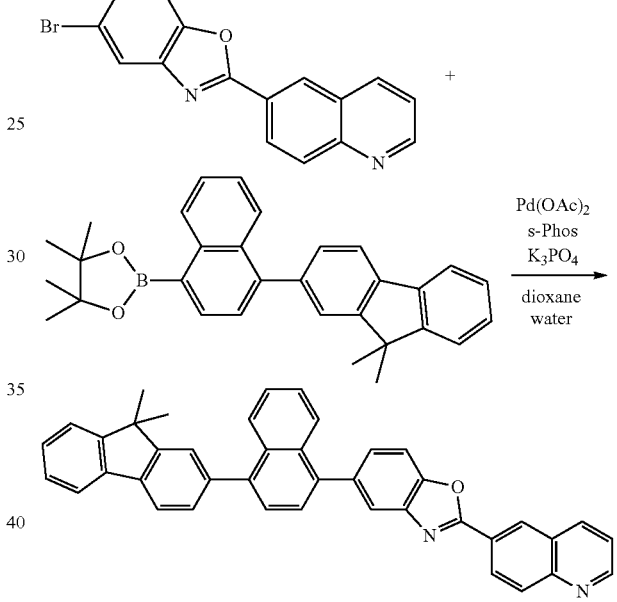

Inside a glove box, Pd(OAc)$_2$ (9.2 mg, 41 µmol) and s-Phos [2-dicyclohexylphosphino-2',6'-dimethoxybiphenyl, available from Aldrich] (33.7 mg, 82.1 µmol) were dissolved in 1,4-dioxane (1 mL). Tripotassium phosphate (5.23 g, 24.6 mmol, 3 eq) was weighed into a 20 mL vial, and 5.16 mL of water was added. 5-Bromo-2-(quinolin-6-yl)benzo[d]oxazole (Precursor 3, 2.67 g, 8.21 mmol) and 2-(4-(9,9-dimethyl-9H-fluoren-2-yl)naphthalen-1-yl)-4,4,5,5-tetramethyl-1,3,2-dioxaborolane (4.40 g, 9.85 mmol, 1.2 eq, the synthesis of this boronic ester is known in the art, e.g. WO2009139499A1) were dissolved in 33 mL of 1,4-dioxane, and the aqueous tripotassium phosphate solution was added, followed by the catalyst solution. The reaction was stirred at room temperature overnight. The reaction was worked up by adding chloroform and water, until both phases appeared clear. The chloroform phase was separated, the aqueous phase re-extracted with chloroform, and the combined organic phases were dried over magnesium sulfate, and treated with activated charcoal. The mixture was filtered through a short plug of silica and basic alumina, and rotovapped to dryness. The residue was purified by flash column chromatography, using a 220 g normal phase silica cartridge (Grace), and a gradient of 0-12% ethyl acetate in toluene. The TLC-pure fractions were collected, and the solvent removed under reduced pressure. The glassy residue was dissolved in a small amount of toluene (~30-50 mL), and hexane was slowly added just before the precipitation point. The solution was left over night for crystallization.

The crystals were isolated by filtration, and dried under high vacuum, at 45° C., over night. The product was received in form of colorless microcrystals (2.92 g, 5.67 mmol, \69.1%, purity: 99.8% by HPLC). A second batch (0.76 g, 1.48 mmol, 18.1%, purity: 99.6% by HPLC) was obtained by complete evaporation of the mother liquor, re-dissolution in a minimal amount of toluene, and by the addition of hexane to just before the precipitation point. The compounds were further purified by sublimation, which brought the purities of the batches to 99.8% and 99.7%, respectively. $^1$H-NMR (500 MHz, CDCl$_3$) δ 9.01 (dd, J=4.2, 1.7 Hz, 1H), 8.82 (d, J=1.9 Hz, 1H), 8.62 (dd, J=8.8, 1.9 Hz, 1H), 8.32 (ddd, J=8.6, 1.6, 0.7 Hz, 1H), 8.28 (dd, J=8.8, 0.8 Hz, 1H), 8.09 (ddt, J=6.8, 3.3, 1.7 Hz, 1H), 8.04-7.97 (m, 2H), 7.86 (dd, J=7.7, 0.6 Hz, 1H), 7.83-7.77 (m, 1H), 7.76 (dd, J=8.2, 0.6 Hz, 1H), 7.63 (dd, J=1.6, 0.6 Hz, 1H), 7.62-7.42 (m, 8H), 7.42-7.31 (m, 2H), 1.57 (s, 6H); $^{13}$C-NMR (126 MHz, CDCl$_3$) δ 27.24, 47.01, 110.33, 119.79, 120.10, 121.64, 122.11, 122.66, 124.52, 125.23, 125.99, 126.05, 126.33, 126.54, 126.58, 126.91, 127.07, 127.34, 127.72, 127.91, 128.00, 128.09, 129.04, 130.55, 132.15, 132.22, 136.87, 137.95, 138.48, 138.95, 139.16, 139.73, 140.57, 142.42, 149.56, 150.44, 152.06, 153.81, 153.89, 163.10; ESI/LC/MS/MS: m/z=565 (base peak, [M+H]$^+$), fragmenting into 549, 129, 155, 352. CLogP: 11.32 (ChemBioDraw Ultra, Version 12.0.2.1076, CambridgeSoft 2010). Additional computed data: HOMO: −5.41 eV, LUMO: −1.92 eV, Triplet Energy: 2.47 eV.

1,3-Bis(2-(quinolin-6-yl)benzo[d]oxazol-5-yl)benzene (Compound 4)

purified via column chromatography, using an "80 g silica cartridge" and a "2% methanol in chloroform isocratic gradient." The pure fractions were combined, concentrated, and dried under high vacuum. The compound was received in form of a colorless glass (organic purity: 99.3%). Sublimation on a train sublimator increased the organic purity to 99.6% (1.40 g, 2.47 mmol, 16.1%, colorless microcrystals). $^1$H-NMR (500 MHz, CDCl$_3$) δ 9.02 (dd, J=4.2, 1.7 Hz, 2H), 8.81 (d, J=2.0 Hz, 2H), 8.61 (dd, J=8.9, 2.0 Hz, 2H), 8.37-8.30 (m, 2H), 8.27 (d, J=8.9 Hz, 2H), 8.14-8.07 (m, 2H), 7.96-7.90 (m, 1H), 7.78-7.58 (m, 7H), 7.52 (dd, J=8.2, 4.2 Hz, 2H); $^{13}$C-NMR (126 MHz, CDCl$_3$) δ 110.82, 118.79, 122.13, 125.17, 125.23, 126.52, 126.79, 127.72, 128.01, 128.07, 129.54, 130.55, 136.89, 138.58, 141.71, 142.91, 149.55, 150.68, 152.09, 163.12; ESI/LC/MS/MS: m/z=567 (base peak, [M+H]$^+$), fragmenting into 567, 385, 203, 202, 129, 155, 231. CLogP: 8.434. (ChemBioDraw Ultra, Version 12.0.2.1076, Cambridge-Soft 2010). Additional computed data: HOMO: −5.90 eV, LUMO: −1.93 eV, Triplet Energy: 2.42 eV.

General Synthetic Approach Toward Further Useful Compounds

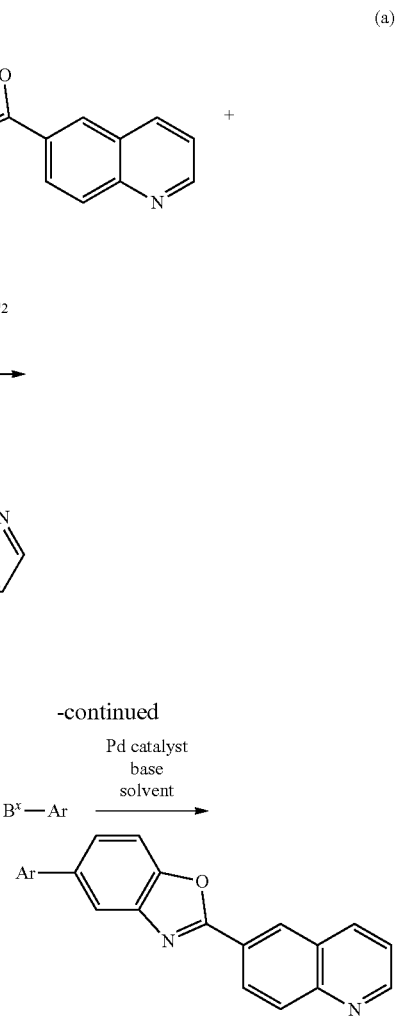

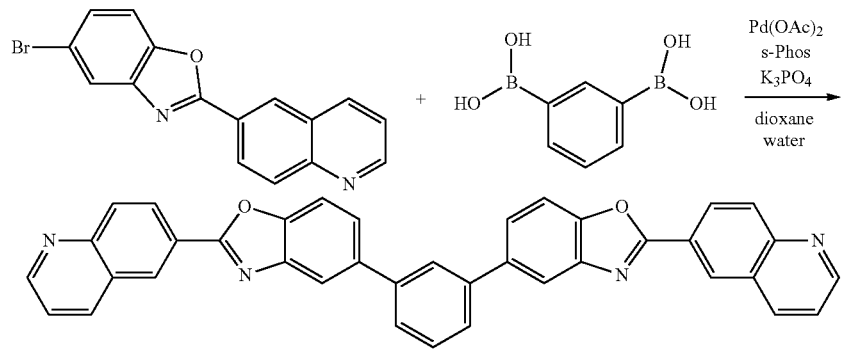

Inside a glove box, Pd(OAc)$_2$ (17.3 mg, 76.9 µmol) and s-Phos [2-dicyclohexylphosphino-2',6'-dimethoxybiphenyl, available from Aldrich] (63.1 mg, 154 µmol) were dissolved in 1,4-dioxane (1 mL). Tripotassium phosphate (9.79 g, 46.1 mmol, 3 eq) was weighed into a 20 mL vial, and 8.59 mL of water was added. 5-Bromo-2-(quinolin-6-yl)benzo[d]oxazole (Precursor 3, 5.00 g, 15.38 mmol) and 1,3-phenylenediboronic acid (1.21 g, 7.30 mmol, 0.475 eq) were dissolved in 55 mL of 1,4-dioxane, and the aqueous tripotassium phosphate solution was added, followed by the catalyst solution. The reaction was stirred at 90° C. for five days. The crude reaction mixture was evaporated to dryness, dissolved in 1 L of boiling chloroform, and adsorbed onto silica gel, followed by rotary evaporation of the solvent. The compound was Additional useful compounds can be synthesized as follows. Under nitrogen or inside a nitrogen-purged glove box, a palladium source (typically palladium(II) acetate, allylpalladium(II) chloride dimer, tris(dibenzylideneacetone)dipalladium(0) or palladium(II) chloride) is dissolved with one or two equivalents of a ligand (a phosphine ligand, such as 1,1'-bis(diphenylphosphino)ferrocene, tricyclohexylphosphine, tri(o-tolyl)phosphine, tri-tert-butylphosphine or its salts, tri(2-furyl)phosphine, triphenylphosphine, 2-dicyclohexylphosphino-2',6'-dimethoxybiphenyl, 2-dicyclohexylphosphino-2',6'-dimethoxybiphenyl—available from Aldrich or an N-heterocyclic carbene ligand such as 1,3-bis-(2,6-diisopropylphenyl)imidazolinium chloride, 1,3-diisopropylimidazolium tetrafluoroborate—available from Aldrich) in an appropriate solvent (for example THF, dioxane, dimethoxyethane). Alternatively, a pre-formed palladium catalyst (tetrakis(triphenylphosphine)palladium(0) or [1,1'-bis(diphenylphosphino)ferrocene]-dichloropalladium (II)) may be used instead. 5-Bromo-2-(quinolin-6-yl)benzo[d]oxazole (Precursor 3, 1.0 eq) and an aryl boronic ester or an aryl boronic acid (1.0-1.2 eq) are dissolved in a suitable solvent (for example, THF, dioxane, DME). A base (3 eq, for example tripotassium phosphate, cesium carbonate, sodium hydroxide or triethylamine) is added to the reaction (either dry or dissolved in degassed water). Preformed catalyst or catalyst solution (typically 0.01-5 mol %) is added to the reaction. The reaction is stirred for 1-48 h at room temperature, or depending on reactivity, at temperatures up to reflux. The reaction is worked up in the usual fashion (e.g. addition of chloroform and water, phase separation, drying of the chloroform phase over magnesium sulfate, followed by flash chromatography and, if necessary, recrystallization.

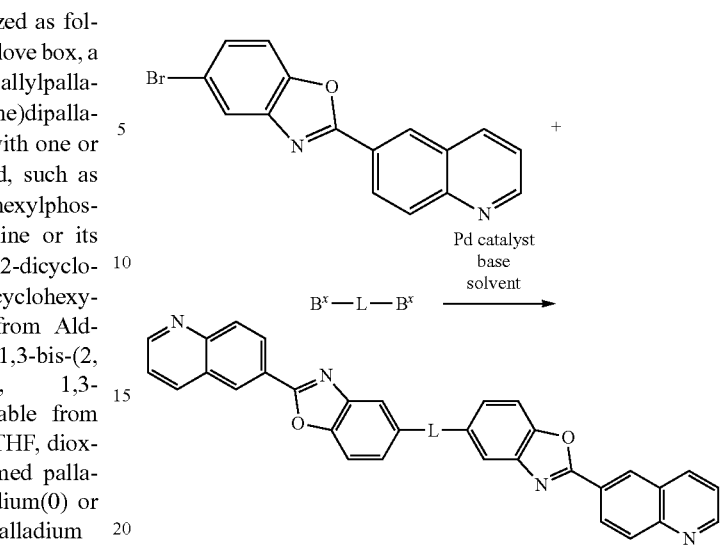

General reaction (b) is performed as described under general reaction (a). 5-Bromo-2-(quinolin-6-yl)benzo[d]oxazole (Precursor 3, 1.9-2.5 eq) and aryl diboronic ester or aryl diboronic acid (1.0 eq) is used in place of the starting materials and quantities used in general reaction (a).

Comparative Examples

The comparative structures in Table A do not have preferred CLogP values and/or preferred Triplet Energy values useful for OLED devices. All of the comparative compounds, except Comparative C, are too hydrophilic for electronic applications, as indicated by their lower CLogP values. The Triplet Energy value for Comparative C is low and not preferred.

TABLE A

| Structure | CLogP | HOMO (eV) | LUMO (eV) | Triplet (eV) |
|---|---|---|---|---|
| Comp. A | 3.508 | | | |
| Comp. B | 3.718 | | | |
| Comp. C | 11.202 | −5.20 | −2.07 | 1.62 |

TABLE A-continued
| Structure | CLogP | HOMO (eV) | LUMO (eV) | Triplet (eV) |
|---|---|---|---|---|
|  Comp. D | 4.326 | | | |
| 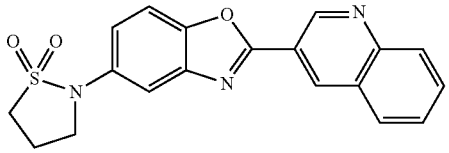 Comp. E | 2.86975 | | | |
| 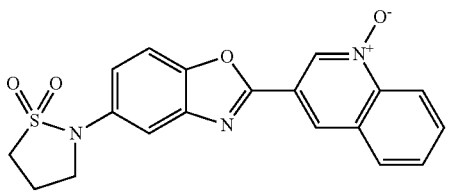 Comp. F | 2.15675 | | | |
| 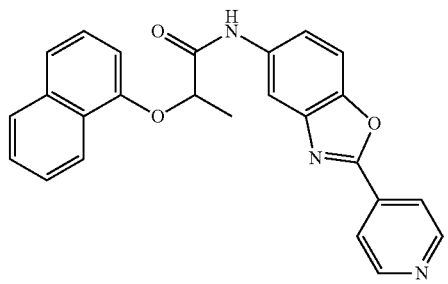 Comp. G | 4.7634 | | | |
| 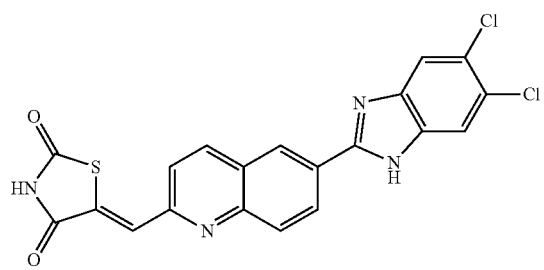 Comp. H | 4.5309 | | | |

OLED Device Fabrication and Testing

All organic materials were purified by sublimation before deposition. OLEDs were fabricated onto an ITO (indium tin oxide) coated glass substrate that served as the anode, and topped with an aluminum cathode. All organic layers were thermally deposited by chemical vapor deposition in a vacuum chamber, with a base pressure of <$10^{-7}$ torr. The deposition rates of organic layers were maintained between 0.1 and 0.05 nm/s. The aluminum cathode was deposited at 0.5 nm/s. The active area of the OLED device was "3 mm×3 mm," as defined by the shadow mask for cathode deposition. The glass substrate (20 mm×20 mm) was available from Samsung Corning with ITO layer thickness of 1500 Ångström.

A five layer film was formed with the following configuration: ITO/hole injection material (HIL): 600 Å/hole transporting material (HTL): 200 Å/fluorescent blue host doped with 2% fluorescent blue dopant (Fl EML): 200 Å/electron transporting material with lithium quinolate (ETL:Liq): 300 Å/electron injection material (EIL): 10 Å/Aluminum. The compounds used in each layer are listed in Table 1.

TABLE 1

| | Name | Commercial Name |
|---|---|---|
| Hole Injection Material | $N^1,N^{1'}$-([1,1'-biphenyl]-4,4'-diyl)bis($N^1$-(naphthalen-1-yl)-$N^4,N^4$-diphenylbenzene-1,4-diamine) | See KR 10-2008-0041682 |
| Hole Transporting Material | $N^4,N^{4'}$-di(naphthalen-1-yl)-$N^4,N^{4'}$-diphenyl-[1,1'-biphenyl]-4,4'-diamine | NPB |
| Fl Blue Host | 9,10-di(naphthalen-2-yl)anthracene | ADN |
| Fl Blue Dopant | (E)-4,4'-(ethene-1,2-diyl)bis(N,N-diphenylaniline) | DPAVB |
| Ref ETL | tris(8-hydroxyquinolinato)aluminum | Alq3 |
| Electron Injection Material | lithium quinolate | Liq |

Each cell, containing HIL, HTL, EML host, EML dopant, ETL, or EIL, was placed inside a vacuum chamber until it reached $10^{-6}$ torr. To evaporate each material, a controlled current was applied to the cell, containing the material, to raise the temperature of the cell. An adequate temperature was applied to keep the evaporation rate of the materials constant throughout the evaporation process.

For the HIL layer, $N^1,N^{1'}$-([1,1'-biphenyl]-4,4'-diyl)bis($N^1$-(naphthalen-1-yl)-$N^4,N^4$-diphenylbenzene-1,4-diamine) was evaporated at a constant 1 Å/s rate, until the thickness of the layer reached 600 Ångström. Simultaneously, the $N^4,N^{4'}$-di(naphthalen-1-yl)-$N^4,N^{4'}$-diphenyl-4', 1'-biphenyl)-4,4'-diamine (NPB) layer was evaporated at a constant 1A/s rate, until the thickness reached 200 Ångström. For the EML layer, 9,10-di(naphthalen-2-yl)anthracene (ADN, host) and (E)-4,4'-(ethene-1,2-diyl)bis(N,N-diphenylaniline) (DPAVB, dopant) were co-evaporated, until the thickness reached 350 Ångström. The deposition rate for host material was 0.98 Å/s, and the deposition for the dopant material was 0.02 Å/s, resulting in a 2% doping of the host material. For the ETL layer, in separate devices, either compound 1, compound 2, compound 3 or compound 4 were each co-evaporated with lithium quinolate(Liq), until the thickness reached 300 Ångström. The evaporation rate for each of compounds 1, 2, 3 or 4 was 0.5 Å/s, and the evaporation rate for Liq was 0.5 Å/s. Alq3 was used as a reference material to compare with compounds 1, 2, 3, or 4. Alq3 was evaporated solely at 1 Å/s rate, until the thickness reached 300 Ångstöm. Finally, "20 Ångström" of a thin electron injection layer (Liq) was evaporated at a 0.2 Å/s rate.

The current-voltage-brightness (J-V-L) characterizations for the OLED devices were performed with a source measurement unit (KEITHLY 238) and a luminescence meter (MINOLTA CS-100A). EL spectra of the OLED devices were collected using a calibrated CCD spectrograph.

Results

Several quinoline-6-benzoxazole-based ETLs used in the inventive film were synthesized in high purity required for OLED device testing. Compound 1, compound 2, compound 3 and compound 4 were each tested in fluorescent blue OLEDs. The results are shown in Table 2 below. The inventive film containing an ETL (Electron Transfer Layer) film layer containing compound 1, compound 2, compound 3 or compound 4, showed better (lower) "turn on voltage" and better (higher) luminous efficiency than the reference example.

TABLE 2

| | Voltage @ 1000 nit [V] | Current Density @ 1000 nit [mA/cm2] | Luminous Efficiency @ 1000 nit [Cd/A] | CIE (X, Y) |
|---|---|---|---|---|
| Alq3 (ref) | 6.5 | 21.4 | 4.9 | 149, 150 |
| Compound 1: Liq | 5.5 | 14.3 | 7.2 | 148, 146 |
| Compound 2: Liq | 5.8 | 11.8 | 6.5 | 148, 146 |
| Compound 3: Liq | 6.0 | 21.6 | 6.5 | 148, 148 |
| Compound 4: Liq | 4.7 | 14.2 | 7.0 | 148, 146 |

The invention claimed is:

1. A composition comprising at least one compound selected from the following Formulas A, B1, B2, B3, B4 or C:

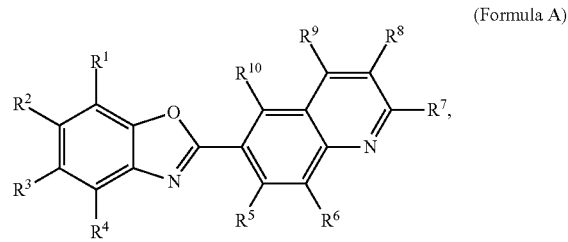

(Formula A)

A)

wherein R1, R2, R3, R4, R5, R6, R7, R8, R9 and R10 are each, independently, selected from the following: a) hydrogen atom; b) a deuterium atom; c) a (C1-C30) alkyl group; d) a substituted (C1-C30) alkyl group; e) a (C6-C50) aryl group; f) a substituted (C6-C50) aryl group; g) a (C3-C50) heteroaryl group; h) a substituted (C3-C50) heteroaryl group; i) a (C3-C30) cycloalkyl group; j) a substituted (C3-C30) cycloalkyl group; or k) a group represented by —(Ar$_1$)$_m$—(Ar$_2$), wherein Ar$_1$ is selected from the group consisting of the following: a substituted or unsubstituted (C5-C30) arylene group, and a substituted or unsubstituted (C5-C30) heteroarylene group, and Ar₂ is selected from the group consisting of the following: a substituted or unsubstituted (C5-C30) aryl group, a substituted or unsubstituted (C5-C30) aryloxy group, and a substituted or unsubstituted (C4-C30) heteroaryl group m is an integer from 0 to 5, and —(Ar₁)ₘ— groups in —(Ar₁)ₘ—(Ar₂) are identical or different from one another;

and with the proviso that at least one of R1, R2, R3, and R4 comprises at least 10 carbon atoms and one cyclic aromatic ring;

and wherein, optionally, two or more R groups selected from R1, R2, R3, R4, R5, R6, R7, R8, R9 and R10 may form one or more ring structures;

and with the proviso that none of R1, R2, R3, R4, R5, R6, R7, R8, R9 and R10 comprise a hydroxyl, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety;

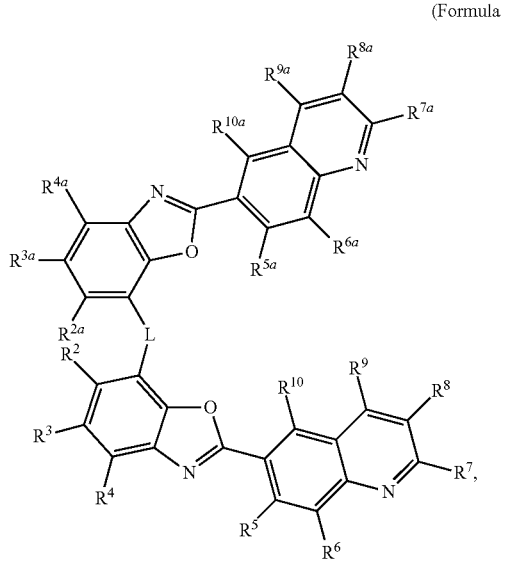

(Formula B1)

B1)

wherein R2, R3, R4, R5, R6, R7, R8, R9, R10, R2a, R3a, R4a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and wherein, optionally, two or more R groups selected from R2, R3, R4, R5, R6, R7, R8, R9 and R10 may form one or more ring structures;

and wherein, optionally, two or more R groups selected from R2a, R3a, R4a, R5a, R6a, R7a, R8a, R9a and R10a may form one or more ring structures;

and with the proviso that none of R2, R3, R4, R5, R6, R7, R8, R9, R10, R2a, R3a, R4a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom;

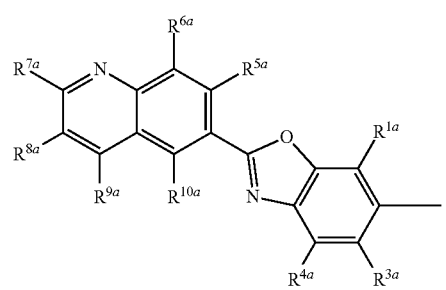

(Formula B2)

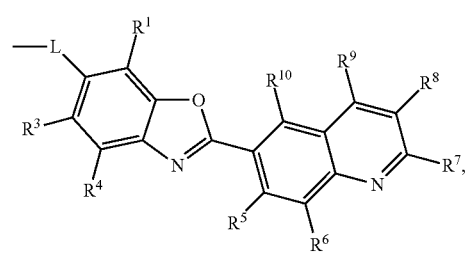

B2)

wherein R1, R3, R4, R5, R6, R7, R8, R9, R10, R1a, R3a, R4a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and wherein, optionally, two or more R groups selected from R1, R3, R4, R5, R6, R7, R8, R9 and R10 may form one or more ring structures;

and wherein, optionally, two or more R groups selected from R1a, R3a, R4a, R5a, R6a, R7a, R8a, R9a and R10a may form one or more ring structures;

and with the proviso that none of R1, R3, R4, R5, R6, R7, R8, R9, R10, R1a, R3a, R4a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom;

(Formula B3)

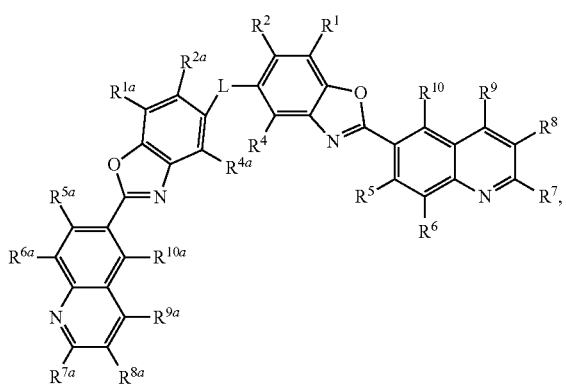

B3)
wherein R1, R2, R4, R5, R6, R7, R8, R9, R10, R1a, R2a, R4a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and wherein, optionally, two or more R groups selected from R1, R2, R4, R5, R6, R7, R8, R9 and R10 may form one or more ring structures;

and wherein, optionally, two or more R groups selected from R1a, R2a, R4a, R5a, R6a, R7a, R8a, R9a and R10a may form one or more ring structures;

and with the proviso that none of R1, R2, R4, R5, R6, R7, R8, R9, R10, R1a, R2a, R4a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom;

(Formula B4)

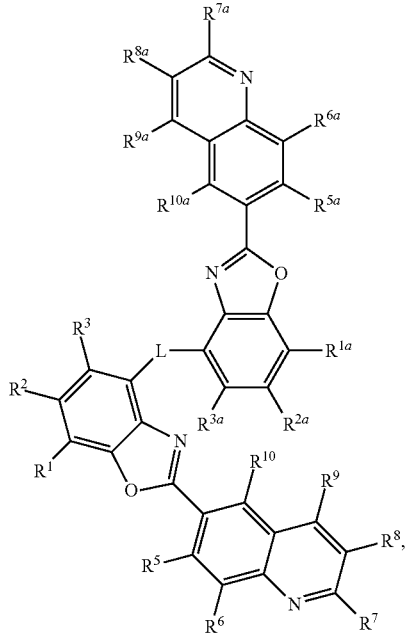

B4)
wherein R1, R2, R3, R5, R6, R7, R8, R9, R10, R1a, R2a, R3a, R5a, R6a, R7a, R8a, R9a, and R10a are each, independently, selected from the following: a) a hydrogen atom, b) a deuterium atom, c) a (C1-C30) alkyl group, d) a substituted (C1-C30) alkyl group, e) a (C6-C50) aryl group, f) a substituted (C6-C50) aryl group, g) a (C3-C50) heteroaryl group, h) a substituted (C3-C50) heteroaryl group, i) a (C3-C30) cycloalkyl group, or j) a substituted (C3-C30) cycloalkyl group;

and wherein, optionally, two or more R groups selected from R1, R2, R3, R5, R6, R7, R8, R9 and R10 may form one or more ring structures;

and wherein, optionally, two or more R groups selected from Ra1, R2a, R3a, R5a, R6a, R7a, R8a, R9a and R10a may form one or more ring structures;

and with the proviso that none of R1, R2, R3, R5, R6, R7, R8, R9, R10, R1a, R2a, R3a, R5a, R6a, R7a, R8a, R9a, and R10a comprise an OH, nitrile, isonitrile, sulfone, sulfonamide, primary amine, secondary amine, quaternary ammonium, amide, thioamide, halogen, a bicyclic moiety containing sulfur, thiazolidinedione, thioxothiazolidinone, or a benzoxazole moiety; and wherein L is a linking group comprising at least one carbon atom; or C) a combination thereof.

2. The composition of claim 1, wherein the at least one compound is selected from Formula A or Formula B3.

3. The composition of claim 1, wherein the at least one compound is selected from Formula A.

4. The composition of claim 3, wherein, for Formula A, each of R5, R6, R7, R8, R9 and R10 is hydrogen.

5. The composition of claim 3, wherein, for Formula A, each of R1, R2, R3, R4, R5, R6, R7, R8, R9 and R10 is, independently, hydrogen or selected from the following substituents:

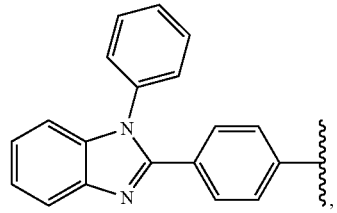

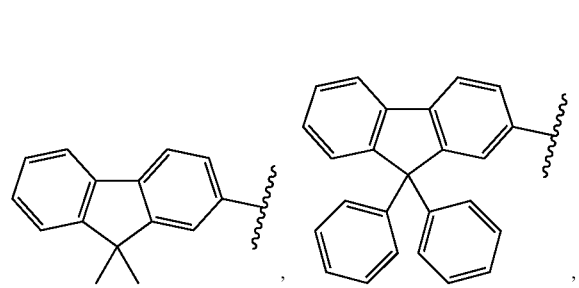

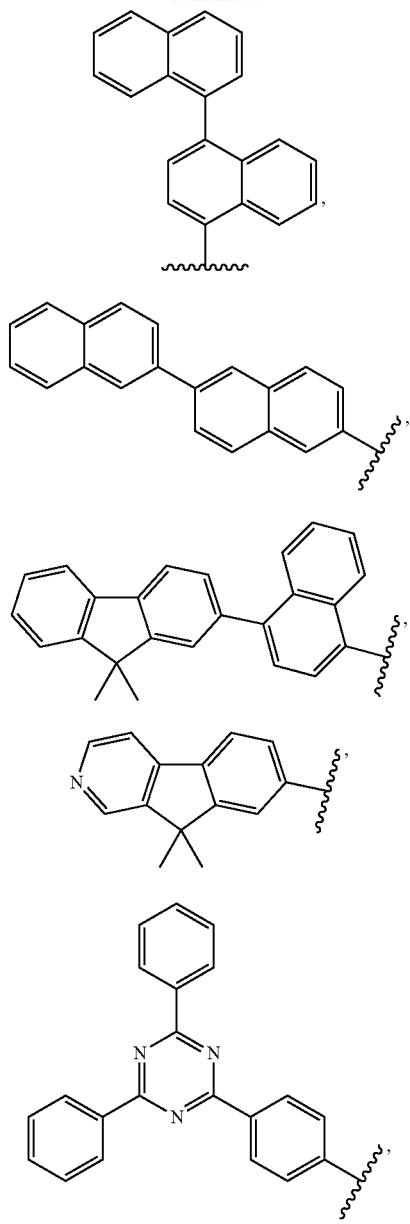
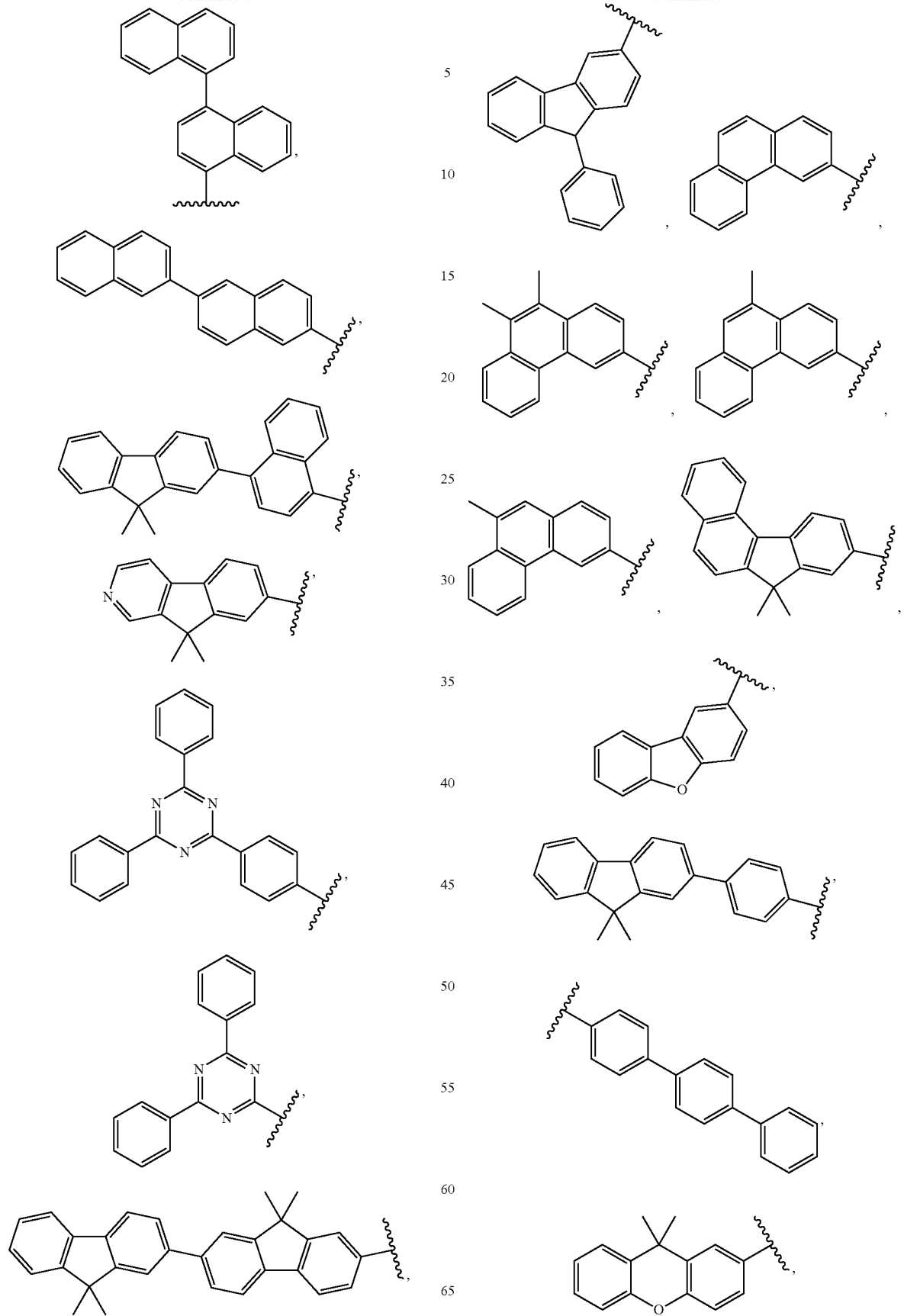

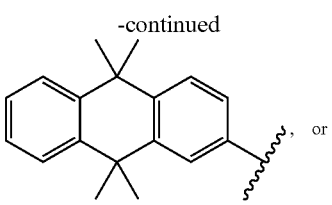, or

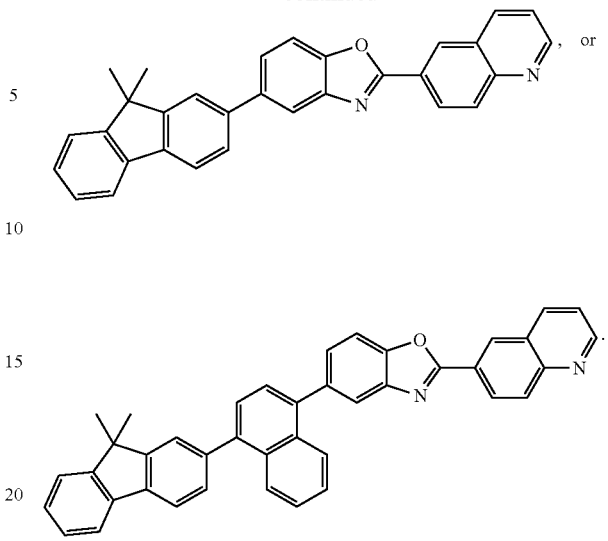, or and with the proviso that at least one of R1, R2, R3, R4, R5, R6, R7, R8, R9, and R10 is not hydrogen.

6. The composition of claim 3, wherein the compound of Formula A is selected from the following:

7. The composition of claim 1, wherein the at least one compound is selected from Formula B3.

8. The composition of claim 7, wherein the compound of Formula B3 is selected from the following:

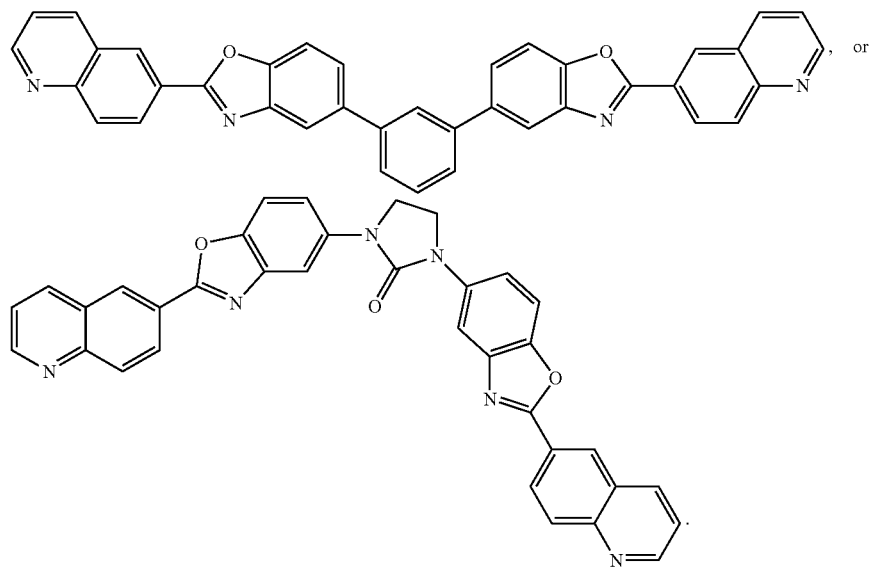

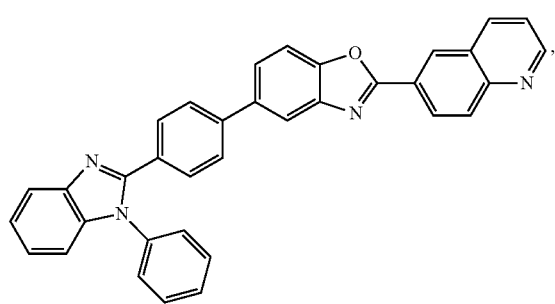

9. The composition of claim 1, wherein the at least one compound is selected from Formula B1.

10. The composition of claim 1, wherein the at least one compound is selected from Formula B2.

11. The composition of claim 1, wherein the at least one compound is selected from Formula B4.

12. The composition of claim 1, wherein the at least one compound has a CLogP value greater than 6.4.

13. The composition of claim 1, wherein the at least one compound has a Triplet Energy level from 1.9 eV to 4.0 eV.

14. A film comprising at least one layer formed from the composition claim 1.

15. An electronic device comprising at least one component formed from the composition of claim 1.

* * * * *